United States Patent
Zhang et al.

(10) Patent No.: US 10,544,467 B2
(45) Date of Patent: **\*Jan. 28, 2020**

(54) SOLID TUMOR METHYLATION MARKERS AND USES THEREOF

(71) Applicants: YouHealth Oncotech, Limited, Grand Cayman (KY); The Regents of the University of California, Oakland, CA (US)

(72) Inventors: Kang Zhang, San Diego, CA (US); Rui Hou, Shenyang (CN); Lianghong Zheng, Pujiangyuan (CN)

(73) Assignees: YouHealth Oncotech, Limited, Grand Cayman (KY); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/839,318

(22) Filed: Dec. 12, 2017

(65) Prior Publication Data

US 2018/0094325 A1  Apr. 5, 2018

Related U.S. Application Data

(63) Continuation of application No. PCT/US2017/040963, filed on Jul. 6, 2017.

(60) Provisional application No. 62/358,795, filed on Jul. 6, 2016.

(51) Int. Cl.
| | |
|---|---|
| *C12Q 1/6886* | (2018.01) |
| *G16B 40/00* | (2019.01) |
| *G16B 20/00* | (2019.01) |
| *C12Q 1/6832* | (2018.01) |

(52) U.S. Cl.
CPC ......... *C12Q 1/6886* (2013.01); *C12Q 1/6832* (2013.01); *G16B 20/00* (2019.02); *G16B 40/00* (2019.02); *C12Q 2600/154* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,525,462 A | 6/1996 | Takarada et al. |
| 5,786,146 A | 7/1998 | Herman et al. |
| | (Continued) | |

FOREIGN PATENT DOCUMENTS

| | | |
|---|---|---|
| CN | 108064314 A | 5/2018 |
| TW | I454578 B | 10/2014 |
| | (Continued) | |

OTHER PUBLICATIONS

Carless, M.A. Chapter 10 of "Chromatin Protocols", Methods in Molecular Biology, vol. 1288, Springer, 2015.*

(Continued)

*Primary Examiner* — Diana B Johannsen
(74) *Attorney, Agent, or Firm* — Morris & Foerster LLP

(57) ABSTRACT

Disclosed herein are methods and kits for identifying a subject as having esophagus cancer, pancreatic cancer, or stomach cancer. Also provided herein are methods and kits for generating the methylation profile of a biomarker associated with esophagus cancer, pancreatic cancer, or stomach cancer.

26 Claims, 7 Drawing Sheets
Specification includes a Sequence Listing.

(56) References Cited

U.S. PATENT DOCUMENTS

| | | | |
|---|---|---|---|
| 5,972,602 | A | 10/1999 | Hyland et al. |
| 6,017,704 | A | 1/2000 | Herman et al. |
| 6,033,854 | A | 3/2000 | Kurnit et al. |
| 6,114,117 | A | 9/2000 | Hepp et al. |
| 6,127,120 | A | 10/2000 | Graham et al. |
| 6,180,349 | B1 | 1/2001 | Ginzinger et al. |
| 6,200,756 | B1 | 3/2001 | Herman et al. |
| 6,265,171 | B1 | 7/2001 | Herman et al. |
| 6,306,597 | B1 | 10/2001 | MacEvicz |
| 6,331,393 | B1 | 12/2001 | Laird et al. |
| 6,344,317 | B2 | 2/2002 | Urnovitz |
| 6,448,001 | B2 | 9/2002 | Oku et al. |
| 6,528,632 | B1 | 3/2003 | Catanzariti et al. |
| 6,797,470 | B2 | 9/2004 | Barany et al. |
| 7,011,944 | B2 | 3/2006 | Prudent et al. |
| 7,037,687 | B2 | 5/2006 | Williams et al. |
| 7,083,917 | B2 | 8/2006 | Barany et al. |
| 7,166,434 | B2 | 1/2007 | Barany et al. |
| 7,169,560 | B2 | 1/2007 | Lapidus et al. |
| 7,186,512 | B2 | 3/2007 | Martienssen et al. |
| 7,232,656 | B2 | 6/2007 | Balasubramanian et al. |
| 7,320,865 | B2 | 1/2008 | Barany et al. |
| 7,332,285 | B2 | 2/2008 | Barany et al. |
| 7,364,858 | B2 | 4/2008 | Barany et al. |
| 7,429,453 | B2 | 9/2008 | Barany et al. |
| 7,459,274 | B2 | 12/2008 | Lakey et al. |
| 7,553,627 | B2 | 6/2009 | Laird et al. |
| 7,598,035 | B2 | 10/2009 | Macevicz |
| 7,611,869 | B2 | 11/2009 | Fan |
| 7,645,596 | B2 | 1/2010 | Williams et al. |
| 7,700,324 | B1 | 4/2010 | Issa et al. |
| 7,769,400 | B2 | 8/2010 | Backholm et al. |
| 7,901,880 | B2 | 3/2011 | Jeddeloh et al. |
| 7,910,296 | B2 | 3/2011 | Jeddeloh et al. |
| 8,323,890 | B2 | 12/2012 | Laird et al. |
| 9,984,201 | B2 | 5/2018 | Zhang et al. |
| 10,093,986 | B2 | 10/2018 | Zhang et al. |
| 2005/0069879 | A1 | 3/2005 | Berlin |
| 2008/0261217 | A1 | 10/2008 | Melnikov et al. |
| 2009/0155791 | A1 | 6/2009 | Wojdacz et al. |
| 2010/0009365 | A1 | 1/2010 | Laird et al. |
| 2010/0144836 | A1 | 6/2010 | Van et al. |
| 2011/0287968 | A1 | 11/2011 | Weinhausel et al. |
| 2014/0080715 | A1 | 3/2014 | Lo et al. |
| 2014/0094380 | A1 | 4/2014 | Sherlock et al. |
| 2016/0210403 | A1 | 7/2016 | Zhang et al. |
| 2018/0274039 | A1 | 9/2018 | Zhang et al. |
| 2018/0341745 | A1 | 11/2018 | Zhang et al. |
| 2019/0136327 | A1 | 5/2019 | Zhang et al. |

FOREIGN PATENT DOCUMENTS

| | | | | |
|---|---|---|---|---|
| WO | WO-03064701 | A2 | 8/2003 | |
| WO | WO-2005012578 | A1 | 2/2005 | |
| WO | WO-2005019477 | A2 | 3/2005 | |
| WO | WO-2005111209 | A1 | 11/2005 | |
| WO | WO-2006056480 | A2 | 6/2006 | |
| WO | WO-2009021141 | A1 | 2/2009 | |
| WO | WO-2009049916 | A2 | 4/2009 | |
| WO | WO-2012031329 | A1 | 3/2012 | |
| WO | WO-2012098215 | A1 | 7/2012 | |
| WO | WO-2012104642 | A1 | 8/2012 | |
| WO | WO-2012138609 | A2 | 10/2012 | |
| WO | WO-2012149171 | A1 | 11/2012 | |
| WO | WO-2013033380 | A1 | 3/2013 | |
| WO | WO-2016020551 | A1 * | 2/2016 | ........... C12Q 1/6886 |
| WO | WO-2016115530 | A1 | 7/2016 | |
| WO | WO-2018/009702 | A1 | 1/2018 | |
| WO | WO-2018009707 | A1 | 1/2018 | |
| WO | WO-2018/161031 | A1 | 9/2018 | |

OTHER PUBLICATIONS

Omura, N. and Goggins, M. Int. J. Clin. Exp. Pathol. 2:310 (2009).*
Naumov, V.A. et al. Epigenetics 8(9):921 (Sep. 2013).*
Joubert, B.R. et al. Cancer Epidemiol. Biomarkers Prev. 23(6):1007 (2014).*
Kim, Y. and Kim. D.H. Chapter 8 of "Cancer Epigenetics: Risk Assessment, Diagnosis, Treatment and Prognosis", Methods in Molecular Biology vo. 1238, Springer (2015).*
Bediaga et al. DNA methylation epigenotypes in breast cancer molecular subtype. Breast Cancer Res 12(5):R77 (2010).
Wilhelm-Benartzi et al. Review of processing and analysis methods for DNA methylation array data. BR J Cancer 109(6):1394-1402 (2013).
Abbruzzese et al. Analysis of a diagnostic strategy for patients with suspected tumors of unknown origin. J Clin Oncol 13:2094-2103 (1995).
Abdi et al. Principal component analysis. Wiley Interdisciplinary Reviews: Computational Statistics 2(4):433-459 (2010).
Acevedo et al. Analysis of the mechanisms mediating tumor-specific changes in gene expression in human liver tumors. Cancer Res. 68:2641-2651 (2008).
Akbani et al. A pan-cancer proteomic perspective on the Cancer Genome Atlas. Nat Commun 5:3887 (2014).
Ambatipudi et al. Tobacco smoking-associated genome-wide DNA methylation changes in the EPIC study. Epigenomics 8(5):599-618 (2016).
Baldi et al. Neural networks and principal component analysis: Learning from examples without local minima. Neural networks 2(1):53-58 (1989).
Balic et al. High quality assessment of DNA methylation in archival tissues from colorectal cancer patients using quantitative high-resolution melting analysis. J. Mol. Diagn. 11:102-108 (2009).
Ball et al. Targeted and genome-scale methylomics reveals gene body signatures in human cell lines. Nat. Biotechnol 27:361-368 (2009).
Benjamini e al. Controlling the false discovery rate: a practical and powerful approach to multiple testing. Journal of the Royal Statistical Society. Series B (Methodological). pp. 289-300 (1995).
Best et al. RNA-Seq of Tumor-Educated Platelets Enables Blood-Based Pan-Cancer, Multiclass, and Molecular Pathway Cancer Diagnostics. Cancer cell 28:666-676 (2015).
Bettegowda et al. Detection of Circulating Tumor DNA in Early- and Late-Stage Human Malignancies. Sci. Transl. Med. 6(224):224ra24 (2014).
Bhardwaj et al. Kernel-based machine learning protocol for predicting DNA-binding proteins. Nucleic Acids Res 33(20):6486-6493 (2005).
Bibkova et al. High-throughput DNA methylation profiling using universal bead arrays. Genome Res. 16:383-393 (2006).
Bo et al. New feature subset selection procedures for classification of expression profiles. Genome Biology 3(4):research0017.1-0017.11 (2002).
Brat et al. Comprehensive, integrative genomic analysis of diffuse lower-grade gliomas. N Engl J Med 372(26):2481-2498 (2015).
Breiman. Random Forests. Machine Learning 45:5-32 (2001).
Candiloro et al. Assessing combined methylation-sensitive high resolution melting and pyrosequencing for the analysis of heterogeneous DNA methylation. Epigenetics 6(4):500-507 (2011).
Costello et al. Restriction landmark genome scanning. Meth. Mol Biol 200:53-70 (2002).
Cottrell et al. A real-time PCR assay for DNA-methylation using methylation-specific blockers. Nucleic Acids Res. 32:e10 (2004).
Cottrell et al. Discovery and validation of 3 novel DNA methylation markers of prostate cancer prognosis. J. Urology 177:1753-1758 (2007).
Dees et al. MuSiC: identifying mutational significance in cancer genomes. Genome Res 22(8):1589-1598 (2012).
Degraves et al. High-Sensitivity Quantitative PCR Platform. Biotechniques 34(1):106-115 (2003).
Deiman et al. Characteristics and applications of nucleic acid sequence-based amplification (NASBA). Mol. Biotechnol. 20(2):163-179 (2002).
Deng et al. Targeted bisulfite sequencing reveals changes in DNA methylation associated with nuclear reprogramming. Nat. Biotechnol 27:353-360 (2009).

(56) References Cited

OTHER PUBLICATIONS

Diep et al. Library-free methylation sequencing with bisulfite padlock probes. Nature Methods 9(3):270-272 (2012).
Dudoit et al. Comparison of Discrimination Methods for the Classification of Tumors Using Gene Expression Data. Journal of the American Statistical Association 97:77-87 (2002).
Eads et al. MethyLight: a high-throughput assay to measure DNA methylation. Nucleic Acid Res. 28:e32 (2000).
Egger et al. Epigenetics in human disease and prospects for epigenetic therapy. Nature 429:457-463 (2004).
Ehrlich. DNA methylation in cancer: too much, but also too little. Oncogene 21(35):5400-5413 (2002).
Fackler et al. Quantitative multiplex methylation-specific PCR analysis doubles detection of tumor cells in breast ductal fluid. Clin. Cancer Res. 12(11 Pt 1):3306-3310 (2006).
Fackler et al. Quantitative multiplex methylation-specific PCR assay for the detection of promoter hypermethylation in multiple genes in breast cancer. Cancer Res. 64(13):4442-4452 (2004).
Feinberg et al. The history of cancer epigenetics. Nat Rev Cancer 4(2):143-153 (2004).
Friedman. Regularized Discriminant Analysis. Journal of the American Statistical Association 84:165-175 (1989).
Frommer et al. A genomic sequencing protocol that yields a positive display of 5-methylcytosine residues in individual DNA strands. PNAS USA 89:1827-1831 (1992).
Gebhard et al. Genome-wide profiling of CpG methylation identifies novel targets of aberrant hypermethylation in myeloid leukemia. Cancer Res. 66:6118-6128 (2006).
Gebhard et al. Rapid and sensitive detection of CpG-methylation using methyl-binding (MB)-PCR. Nucleic Acids Res. 34:e82 (2006).
Gibson et al. A novel method for real time quantitative RT-PCR. Genome Research 6:995-1001 (1996).
Gonzalgo et al. Rapid quantitation of methylation differences at specific sites using methylation-sensitive single nucleotide primer extension (Ms-SNuPE). Nucleic Acids Res. 25:2529-2531 (1997).
Grant et al. Molecular and genetic pathways in gliomas: the future of personalized therapeutics. CNS Oncology 3(2):123-136 (2014).
Greco et al. Cancer of unknown primary site. Cancer: Principles and Practice of Oncology. Ed 9. Chapter 137. (pp. 2033-2051) (2011).
Greco et al. Molecular profiling diagnosis in unknown primary cancer: accuracy and ability to complement standard pathology. J Natl Cancer Inst 105(11):782-790 (2013).
Han et al. The Pan-Cancer analysis of pseudogene expression reveals biologically and clinically relevant tumour subtypes. Nat Commun 5:3963 (2014).
Harris et al. Single-molecule DNA sequencing of a viral genome. Science 320:106-109 (2008).
Hearst et al. Support vector machines. Intelligent Systems and their Applications. IEEE 13(4):18-28 (1998).
Herman et al. Gene silencing in cancer in association with promoter hypermethylation. N Engl J Med 349(21):2042-2054 (2003).
Herman et al. Methylation-specific PCR: a novel PCR assay for methylation status of CpG islands. PNAS USA 93:9821-9826 (1996).
Heyn et al. DNA methylation profiling in the clinic: applications and challenges. Nature Reviews Genetics 13(10):679-692 (2012).
Horak et al. ChIP-chip: a genomic approach for identifying transcription factor binding sites. Methods Enzymol 350:469-483 (2002).
Hudson. A new statistic for detecting genetic differentiation. Genetics 155(4):2011-2014 (2000).
Itzkowitz et al. Improved fecal DNA test for colorectal cancer screening. Clin Gastroenterol. Hepatol. 5(1):111-117 (2007).
Jaenisch et al. Epigenetic regulation of gene expression: how the genome integrates intrinsic and environmental signals. Nat Genet 33 Suppl:245-254 (2003).
Kandoth et al. Mutational landscape and significance across 12 major cancer types. Nature 502(7471):333-339 (2013).
Koboldt et al. VarScan 2: somatic mutation and copy number alteration discovery in cancer by exome sequencing. Genome Res 22(3):568-576 (2012).
Koga et al. Genome-wide screen of promoter methylation identifies novel markers in melanoma. Genome Res. 19:1462-1470 (2009).
Kulis et al. DNA methylation and cancer. Adv Genet 70:27-56 (2010).
Langmead et al. Fast gapped-read alignment with Bowtie 2. Nature Methods 9:357-359 (2012).
Li et al. Multiplex padlock targeted sequencing reveals human hypermutable CpG variations. Genome Res 19(9):1606-1615 (2009).
Lieb. Genome-wide mapping of protein-DNA interactions by chromatin immunoprecipitation and DNA microarray hybridization. Methods Mol Biol 224:99-109 (2003).
Liefers et al. Micrometastases and survival in stage II colorectal cancer. N Engl J Med 339(4):223-228 (1998).
Margulies et al. Genome sequencing in microfabricated high-density picolitre reactors. Nature 437:376-380 (2005).
Mazor et al. DNA Methylation and Somatic Mutations Converge on the Cell Cycle and Define Similar Evolutionary Histories in Brain Tumors. Cancer Cell 28(3):307-317 (2015).
McClelland et al. Effect of site-specific modification on restriction endonucleases and DNA modification methyltransferases. Nucleic Acids Res.22(17):3640-3659 (1994).
Morris et al. Who to treat with adjuvant therapy in Dukes B/stage II colorectal cancer? The need for high quality pathology. Gut 56(10):1419-1425 (2007).
Murphy et al. Patterns of Colorectal Cancer Care in the United States: 1990-2010. J Natl Cancer Inst 107(10):11 pgs. (2015).
Nakano et al. Single-molecule PCR using water-in-oil emulsion. J. Biotech. 102:117-124 (2003).
Nolte. Branched DNA signal amplification for direct quantitation of nucleic acid sequences in clinical specimens. Adv. Clin. Chem. 33:201-235 (1998).
O'Geen et al. Comparison of sample preparation methods for ChIP-chip assays. BioTechniques 41(5):577-580 (2006).
Ogino et al. Predictive and prognostic analysis of PIK3CA mutation in stage III colon cancer intergroup trial. J Natl Cancer Inst 105(23):1789-1798 (2013).
O'Shea et al. Cytokine signaling in 2002: new surprises in the Jak/Stat pathway. Cell 109(2):S121-S131 (2002).
Olek et al. The pre-implantation ontogeny of the H19 methylation imprint Nat. Genet. 17(3):275-276 (1997).
Paez et al. EGFR mutations in lung cancer: correlation with clinical response to gefitinib therapy. Science 304(5676):1497-1500 (2004).
PCT/US2016/013716 International Preliminary Report on Patentability dated Jul. 27, 2017.
PCT/US2016/013716 International Search Report and Written Opinion dated May 12, 2016.
Pelizzola et al. MEDME: an experimental and analytical methodology for the estimation of DNA methylation levels based on microarray derived MeDIP-enrichment. Genome Res. 18:1652-1659 (2008).
Pentheroudakis et al. Novel microRNA-based assay demonstrates 92% agreement with diagnosis based on clinicopathologic and management data in a cohort of patients with carcinoma of unknown primary. Mol Cancer 12:57 (2013).
Porreca et al. Multiplex amplification of large sets of human exons. Nature Methods 4(11):931-936 (2007).
Raab et al. Quality in cancer diagnosis. CA Cancer J Clin 60(3):139-165 (2010).
Radmacher et al. A paradigm for class prediction using gene expression profiles. Journal of Computational Biology 9:505-511 (2002).
Ramaswamy et al. Multiclass cancer diagnosis using tumor gene expression signatures. PNAS USA 98:15149-15154 (2001).
Rauch et al. High-resolution mapping of DNA hypermethylation and hypomethylation in lung cancer. PNAS USA 105:252-257 (2008).
Rein et al. Identifying 5-methylcytosine and related modifications in DNA genomes. Nucleic Acids Res. 26(10):2255-2264 (1998).
Ross et al. Comprehensive Genomic Profiling of Carcinoma of Unknown Primary Site: New Routes to Targeted Therapies. JAMA Oncol 1(1):40-49 (2015).
Ruczinski et al. Logic Regression. Journal of Computational and Graphical Statistics 12:475-5111 (2003).

(56) References Cited

OTHER PUBLICATIONS

Sadri et al. Rapid analysis of DNA methylation using new restriction enzyme sites created by bisulfite modification. Nucleic Acids Res. 24:5058-5059 (1996).
Salazar et al. Gene expression signature to improve prognosis prediction of stage II and III colorectal cancer. J Clin Oncol 29(1):17-24 (2011).
Schmoll et al. Capecitabine Plus Oxaliplatin Compared With Fluorouracil/Folinic Acid As Adjuvant Therapy for Stage III Colon Cancer: Final Results of the NO16968 Randomized Controlled Phase III Trial. J Clin Oncol 33(32):3733-3740 (2015).
Shevade et al. A simple and efficient algorithm for gene selection using sparse logistic regression. Bioinformatics 19(17):2246-2253 (2003).
Shiraishi et al. Isolation of DNA fragments associated with methylated CpG islands in human adenocarcinomas of the lung using a methylated DNA binding column and denaturing gradient gel electrophoresis. PNAS USA 96(6):2913-2918 (1999).
Siegel et al. Cancer statistics, 2015. CA Cancer J Clin 65:5-29 (2015).
Simon et al. Pitfalls in the use of DNA microarray data for diagnostic and prognostic classification. Journal of the National Cancer Institute 95:14-18 (2003).
Smith et al. Cancer screening in the United States, 2015: a review of current American cancer society guidelines and current issues in cancer screening. CA Cancer J Clin 65(1):30-54 (2015).
Soni et al. Progress toward ultrafast DNA sequencing using solid-state nanopores. Clin. Chem. 53:1996-2001 (2007).
Sorlie et al. Gene expression patterns of breast carcinomas distinguish tumor subclasses with clinical implications. PNAS USA 98:10869-10874 (2001).
Sultan et al. Stat5 promotes homotypic adhesion and inhibits invasive characteristics of human breast cancer cells. Oncogene 24(5):746-760 (2005).
Thomas et al. The role of JAK/STAT signalling in the pathogenesis, prognosis and treatment of solid tumours. British J Cancer 113(3):365-371 (2015).
Tost et al. DNA methylation analysis by pyrosequencing. Nature Protocols 2:2265-2275 (2007).
Toyota et al. Identification of differentially methylated sequences in colorectal cancer by methylated CpG island amplification. Cancer Res. 59:2307-2312 (1999).
Tran et al. Prolactin inhibits BCL6 expression in breast cancer through a Stat5a-dependent mechanism. Cancer Res 70(4):1711-1721 (2010).
U.S. Appl. No. 14/986,520 Office Action dated Apr. 11, 2017.
U.S. Appl. No. 14/986,520 Office Action dated Jun. 30, 2017.
Ushijima et al. Methylation-Sensitive Representational Difference Analysis (MS-RDA). Methods Mol Biol 507:117-130 (2009).
Vaissiere et al. Epigenetic interplay between histone modifications and DNA methylation in gene silencing. Mutat Res 659(1-2):40-48 (2008).
Varadhachary. New strategies for carcinoma of unknown primary: the role of tissue-of-origin molecular profiling. Clin Cancer Res 19(15):4027-4033 (2013).
Vedeld et al. The novel colorectal cancer biomarkers CDO1, ZSCAN18 and ZNF331 are frequently methylated across gastrointestinal cancers. Int J Cancer 136:844-853 (2015).
Wang et al. Identification and characterization of essential genes in the human genome. Science 350(6264):1096-1101 (2015).
Weber et al. Chromosome-wide and promoter-specific analyses identify sites of differential DNA methylation in normal and transformed human cells. Nat. Genet. 37:853-862 (2005).
Weinstein et al. The Cancer Genome Atlas Pan-Cancer analysis project. Nat Genet 45(10):1113-1120 (2013).
Wojdacz et al. Methylation-sensitive high resolution melting (MS-HRM): a new approach for sensitive and high-throughput assessment of methylation. Nucleic Acids Res. 35(6):e41 (2007).
Wojdacz et al. Methylation-sensitive high-resolution melting. Nature Protocols 3(12):1903-1908 (2008).
Wright et al. A random variance model for detection of differential gene expression in small microarray experiments. Bioinformatics 19(18):2448-2455 (2003).
Xiong et al COBRA: a sensitive and quantitative DNA methylation assay. Nucleic Acids Res. 25:2532-2534 (1997).
Yan et al. IDH1 and IDH2 mutations in gliomas. N Engl J Med 360(8):765-773 (2009).
Yao et al. Inferring regulatory element landscapes and transcription factor networks from cancer methylomes. Genome Biol 16:105 (2015).
Zou et al. Association of Clinical Chemistry (AACC) poster presentation on Jul. 28, 2010. Sensitive Quantification of Methylated Markers with a Novel Methylation Specific Technology. Available at www.exactsciences.com (10 pgs).
Fernandez et al. A DNA methylation fingerprint of 1628 human samples. Genome Res 22(2):407-19 (2012).
PCT/US2017/040963 International Search Report and Written Opinion dated Nov. 8, 2017.
U.S. App. No. 16/315,610, filed Jul. 6, 2017, by Zhang et al. (U.S. Patent Application is not submitted herewith pursuant to the waiver of 37 C.F.R. § 1.98(a)(2)(iii) issued by the Office on Sep. 21, 2004).
U.S. App. No. 16/315,609, filed Jul. 6, 2017, by Zhang et al. (U.S. Patent Application is not submitted herewith pursuant to the waiver of 37 C.F.R. § 1.98(a)(2)(iii) issued by the Office on Sep. 21, 2004).
U.S. App. No. 16/315,608, filed Jul. 6, 2017, by Zhang et al. (U.S. Patent Application is not submitted herewith pursuant to the waiver of 37 C.F.R. § 1.98(a)(2)(iii) issued by the Office on Sep. 21, 2004).
U.S. App. No. 16/315,605, filed Jul. 6, 2017, by Zhang et al. (U.S. Patent Application is not submitted herewith pursuant to the waiver of 37 C.F.R. § 1.98(a)(2)(iii) issued by the Office on Sep. 21, 2004).

* cited by examiner

SOLID TUMOR METHYLATION MARKERS AND USES THEREOF

CROSS-REFERENCE

This application is a continuation of PCT International Application No. PCT/US2017/040963, filed Jul. 6, 2017, which claims the benefit of U.S. Provisional Application No. 62/358,795, filed Jul. 6, 2016, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 16, 2017, is named 49697_711_301_SL.txt and is 800 bytes in size.

BACKGROUND OF THE DISCLOSURE

Cancer is a leading cause of deaths worldwide, with annual cases expected to increase from 14 million in 2012 to 22 million during the next two decades (WHO). In some instances, diagnostic procedures for a solid tumor such as esophagus cancer, pancreatic cancer, or stomach cancer begin only after a patient is already present with symptoms, leading to costly, invasive, and sometimes time-consuming procedures. In addition, inaccessible areas sometimes prevent an accurate diagnosis. Further, high cancer morbidities and mortalities are associated with late diagnosis.

SUMMARY OF THE DISCLOSURE

Provided herein are methods and kits for identifying a subject as having esophagus cancer, pancreatic cancer or stomach cancer.

Provided herein, in certain embodiments, is a method of selecting a subject suspected of having a solid tumor for treatment, the method comprising: (a) processing an extracted genomic DNA with a deaminating agent to generate a genomic DNA sample comprising deaminated nucleotides, wherein the extracted genomic DNA is obtained from a biological sample from the subject suspected of having a solid tumor; (b) generating a methylation profile comprising cg10673833 from the extracted genomic DNA; (c) comparing the methylation profile of the biomarker with a control; (d) identifying the subject as having the solid tumor if the methylation profile correlates to the control; and (e) administering an effective amount of a therapeutic agent to the subject if the subject is identified as having the solid tumor; wherein the solid tumor is selected from esophagus cancer, pancreatic cancer, or stomach cancer.

In some embodiments, the comparing further comprises generating a pair-wise methylation difference dataset comprising: (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

In some embodiments, the comparing further comprises analyzing the pair-wise methylation difference dataset with a control by a machine learning method to generate the methylation profile.

In some embodiments, the first primary cancer sample is an esophagus cancer sample, a pancreatic cancer sample, or a stomach cancer sample.

In some embodiments, the second primary cancer sample is a non-esophagus cancer sample, non-pancreatic cancer sample, or a non-stomach cancer sample.

In some embodiments, the control comprises a set of methylation profiles, wherein each said methylation profile is generated from a biological sample obtained from a known cancer type.

In some embodiments, the known cancer type is esophagus cancer, pancreatic cancer, or stomach cancer.

In some embodiments, the known cancer type is a relapsed or refractory esophagus cancer, a relapsed or refractory pancreatic cancer, or a relapsed or refractory stomach cancer.

In some embodiments, the known cancer type is a metastatic esophagus cancer, a metastatic pancreatic cancer, or a metastatic stomach cancer.

In some embodiments, the machine learning method utilizes an algorithm selected from one or more of the following: a principal component analysis, a logistic regression analysis, a nearest neighbor analysis, a support vector machine, and a neural network model.

In some embodiments, the generating further comprises hybridizing the biomarker with a probe, and performing a DNA sequencing reaction to quantify the methylation of the biomarker.

In some embodiments, the biological sample comprises circulating tumor cells.

In some embodiments, the subject is a human.

In certain embodiments, provided herein is a method of generating a methylation profile of a biomarker in a subject in need thereof, comprising: (a) processing an extracted genomic DNA with a deaminating agent to generate a genomic DNA sample comprising deaminated nucleotides, wherein the extracted genomic DNA is obtained from a biological sample from the subject; (b) detecting a hybridization between the extracted genomic DNA and a probe, wherein the probe hybridizes to cg10673833; and (c) generating a methylation profile based on the detected hybridization between the extracted genomic DNA and the probe.

In some embodiments, the generating further comprises generating a pair-wise methylation difference dataset comprising: (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

In some embodiments, the generating further comprises analyzing the pair-wise methylation difference dataset with a control by a machine learning method to generate the methylation profile.

In some embodiments, the first primary cancer sample is an esophagus cancer sample, a pancreatic cancer sample, or a stomach cancer sample.

In some embodiments, the second primary cancer sample is a non-esophagus cancer sample, non-pancreatic cancer sample, or a non-stomach cancer sample.

In some embodiments, the control comprises a set of methylation profiles, wherein each said methylation profile is generated from a biological sample obtained from a known cancer type.

In some embodiments, the known cancer type is esophagus cancer, pancreatic cancer, or stomach cancer.

In some embodiments, the known cancer type is a relapsed or refractory esophagus cancer, a relapsed or refractory pancreatic cancer, or a relapsed or refractory stomach cancer.

In some embodiments, the known cancer type is a metastatic esophagus cancer, a metastatic pancreatic cancer, or a metastatic stomach cancer.

In some embodiments, the known cancer type is esophagus cancer. In some embodiments, esophagus cancer comprises esophageal squamous cell carcinoma, esophageal adenocarcinoma, or undifferentiated esophagus cancer.

In some embodiments, the known cancer type is pancreatic cancer. In some embodiments, pancreatic cancer comprises exocrine pancreatic cancers and pancreatic endocrine tumors. In some embodiments, pancreatic cancer comprises pancreatic adenocarcinoma, pancreatic adenosquamous carcinomas, pancreatic squamous cell carcinomas, signet ring cell carcinomas, undifferentiated pancreatic carcinomas, undifferentiated pancreatic carcinomas with giant cells, ampullary cancer, gastrinomas, insulinomas, glucagonomas, somatostatinomas, VIPomas, PPomas, or carcinoid tumor.

In some embodiments, the known cancer type is stomach cancer. In some embodiments, stomach cancer comprises gastric adenocarcinoma, lymphoma of the stomach, gastrointestinal stromal tumor, carcinoid tumor, primary squamous cell carcinoma of stomach, gastric small-cell carcinoma, or leiomyosarcoma of the stomach.

In some embodiments, the machine learning method utilizes an algorithm selected from one or more of the following: a principal component analysis, a logistic regression analysis, a nearest neighbor analysis, a support vector machine, and a neural network model.

In some embodiments, the method further comprises performing a DNA sequencing reaction to quantify the methylation of the biomarker prior to generating the methylation profile. In some embodiments, the biological sample comprises circulating tumor cells.

In some embodiments, the subject is a human.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2A shows a scatter plot of the methylation rate. FIG. 2B shows a boxplot of the methylation rate.

FIG. 3A shows a scatter plot of the methylation rate. FIG. 3B shows a boxplot of the methylation rate.

FIG. 4A shows a scatter plot of the methylation rate. FIG. 4B shows a boxplot of the methylation rate.

DETAILED DESCRIPTION OF THE DISCLOSURE

Figure 1:
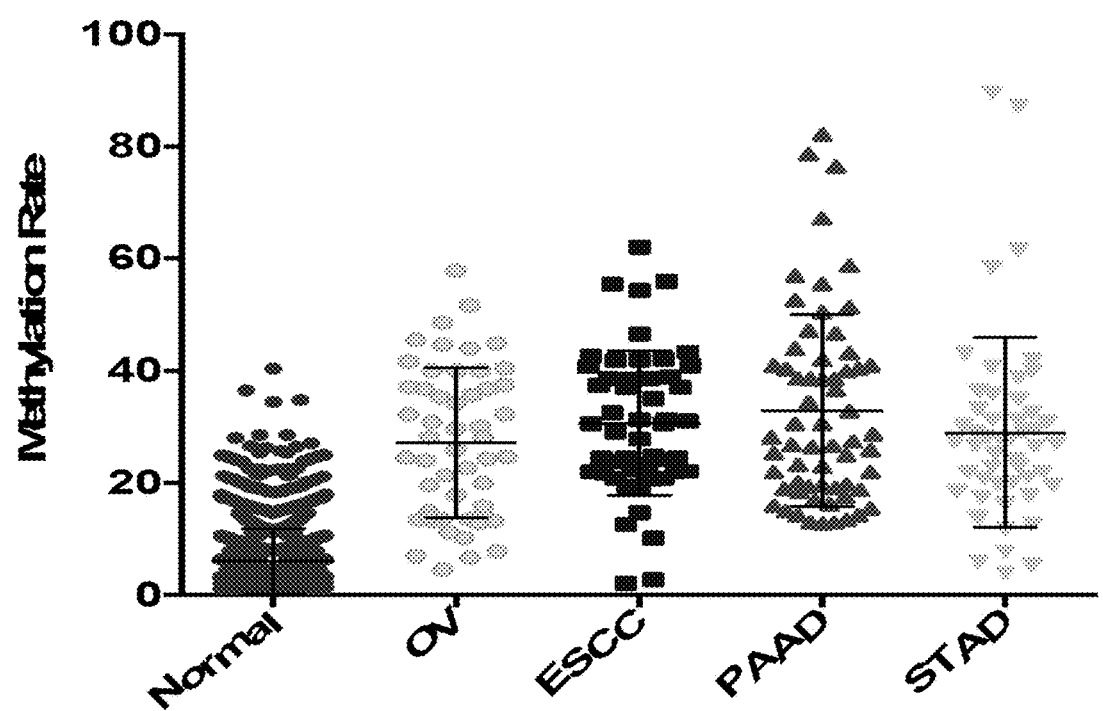
FIG. 1 illustrates the methylation rate of cell-free DNA (cfDNA) in different cancer types.

Cancer is characterized by an abnormal growth of a cell caused by one or more mutations or modifications of a gene leading to dysregulated balance of cell proliferation and cell death. DNA methylation silences expression of tumor suppression genes, and presents itself as one of the first neoplastic changes. Methylation patterns found in neoplastic tissue and plasma demonstrate homogeneity, and in some instances are utilized as a sensitive diagnostic marker. For example, cMethDNA assay has been shown in one study to be about 91% sensitive and about 96% specific when used to diagnose metastatic breast cancer. In another study, circulating tumor DNA (ctDNA) was about 87.2% sensitive and about 99.2% specific when it was used to identify KRAS gene mutation in a large cohort of patients with metastatic colon cancer (Bettegowda et al., Detection of Circulating Tumor DNA in Early- and Late-Stage Human Malignancies. Sci. Transl. Med, 6(224):ra24. 2014). The same study further demonstrated that ctDNA is detectable in >75% of patients with advanced pancreatic, ovarian, colorectal, bladder, gastroesophageal, breast, melanoma, hepatocellular, and head and neck cancers (Bettegowda et al).

Additional studies have demonstrated that CpG methylation pattern correlates with neoplastic progression. For example, in one study of breast cancer methylation patterns, P16 hypermethylation has been found to correlate with early stage breast cancer, while TIMP3 promoter hypermethylation has been correlated with late stage breast cancer. In addition, BMP6, CST6 and TIMP3 promoter hypermethylation have been shown to associate with metastasis into lymph nodes in breast cancer.

In some embodiments, DNA methylation profiling provides higher clinical sensitivity and dynamic range compared to somatic mutation analysis for cancer detection. In other instances, altered DNA methylation signature has been shown to correlate with the prognosis of treatment response for certain cancers. For example, one study illustrated that in a group of patients with advanced rectal cancer, ten differentially methylated regions were used to predict patients' prognosis. Likewise, RASSF1A DNA methylation measurement in serum was used to predict a poor outcome in patients undergoing adjuvant therapy in breast cancer patients in a different study. In addition, SRBC gene hypermethylation was associated with poor outcome in patients with colorectal cancer treated with oxaliplatin in a different study. Another study has demonstrated that ESR1 gene methylation correlate with clinical response in breast cancer patients receiving tamoxifen. Additionally, ARHI gene promoter hypermethylation was shown to be a predictor of long-term survival in breast cancer patients not treated with tamoxifen.

In some embodiments, disclosed herein are methods and kits of diagnosing esophagus cancer, pancreatic cancer or stomach cancer based on DNA methylation profiling. In some instances, also provided herein are methods and kits of identifying a subject has having esophagus cancer, pancreatic cancer or stomach cancer based on the DNA methylation profiling.

Methods of Use

Methods of Diagnosis of a Subject

Disclosed herein, in certain embodiments, are methods of diagnosing esophagus cancer, pancreatic cancer or stomach cancer and selecting subjects suspected of having esophagus cancer, pancreatic cancer or stomach cancer for treatment. In some instances, the methods comprise utilizing one or more biomarkers described herein. In some instances, a biomarker comprises a cytosine methylation site. In some instances, cytosine methylation comprises 5-methylcytosine (5-mCyt) and 5-hydroxymethylcytosine. In some cases, a cytosine methylation site occurs in a CpG dinucleotide motif. In other cases, a cytosine methylation site occurs in a CHG or CHH motif, in which H is adenine, cytosine or thymine. In some instances, one or more CpG dinucleotide motif or CpG site forms a CpG island, a short DNA sequence rich in CpG dinucleotide. In some instances, CpG islands are typically, but not always, between about 0.2 to about 1 kb in length. In some instances, a biomarker comprises a CpG island.

In some embodiments, disclosed herein is a method of selecting a subject suspected of having a solid tumor for treatment, in which the method comprises (a) processing an extracted genomic DNA with a deaminating agent to generate a genomic DNA sample comprising deaminated nucleotides, wherein the extracted genomic DNA is obtained from a biological sample from the subject suspected of having a solid tumor; (b) generating a methylation profile comprising biomarker cg10673833 from the extracted genomic DNA; (c) comparing the methylation profile of the biomarker with a control; (d) identifying the subject as having the solid tumor if the methylation profile correlates to the control; and (e) administering an effective amount of a therapeutic agent to the subject if the subject is identified as having the solid tumor, wherein the solid tumor is selected from esophagus cancer, pancreatic cancer or stomach cancer.

In some embodiments, a methylation profile comprises a plurality of CpG methylation data for one or more biomarkers described herein. In some instances, a plurality of CpG methylation data is generated by first obtaining a genomic DNA (e.g., nuclear DNA or circulating DNA) from a biological sample, and then treating the genomic DNA by a deaminating agent to generate an extracted genomic DNA. In some instances, the extracted genomic DNA (e.g., extracted nuclear DNA or extracted circulating DNA) is optionally treated with one or more restriction enzymes to generate a set of DNA fragments prior to submitting for sequencing analysis to generate CpG methylation data. In some cases, the sequencing analysis comprises hybridizing each of the one or more biomarkers described herein with a probe, and performing a DNA sequencing reaction to quantify the methylation of each of the one or more biomarkers. In some instances, the CpG methylation data is then input into a machine learning/classification program to generate a methylation profile.

In some instances, a set of biological samples are generated and subsequently input into the machine learning/classification program. In some instances, the set of biological samples comprises 2, 3, 4, 5, 6, 7, 8, 9, 10, 20, 30, or more biological samples. In some instances, the set of biological samples comprises 2, 3, 4, 5, 6, 7, 8, 9, 10, 20, 30, or more normal biological samples. In some instances, the set of biological samples comprises 2, 3, 4, 5, 6, 7, 8, 9, 10, 20, 30, or more cancerous biological samples. In some cases, the set of biological samples comprise a biological sample of interest, a first primary cancer sample, a second primary cancer sample, a first normal sample, a second normal sample, and a third normal sample; wherein the first, and second primary cancer samples are different; and wherein the first, second, and third normal samples are different. In some cases, three pairs of difference datasets are generated in which the three pairs of dataset comprise: a first difference dataset between the methylation profile of the biological sample of interest and the first normal sample, in which the biological sample of interest and the first normal sample are from the same biological sample source; a second difference dataset between a methylation profile of a second normal sample and a methylation profile of a third normal sample, in which the second and third normal samples are different; and a third difference dataset between a methylation profile of a first primary cancer sample and a methylation profile of a second primary cancer sample, in which the first and second primary cancer samples are different. In some instances, the difference datasets are further input into the machine learning/classification program. In some cases, a pair-wise methylation difference dataset from the first, second, and third datasets is generated and then analyzed in the presence of a control dataset or a training dataset by the machine learning/classification method to generate the cancer CpG methylation profile. In some instances, the first primary cancer sample is an esophagus cancer sample, a pancreatic cancer sample, or a stomach cancer sample. In some cases, the second primary cancer sample is a non-esophagus cancer sample, non-pancreatic cancer sample, or a non-stomach cancer sample. In some cases, the machine learning method comprises identifying a plurality of markers and a plurality of weights based on a top score (e.g., a t-test value, a $\beta$ test value), and classifying the samples based on the plurality of markers and the plurality of weights. In some cases, the machine learning method utilizes an algorithm selected from one or more of the following: a principal component analysis, a logistic regression analysis, a nearest neighbor analysis, a support vector machine, and a neural network model.

In some embodiments, the CpG methylation profile comprises biomarker cg10673833.

In some instances, the subject is diagnosed in having esophagus cancer, pancreatic cancer, or stomach cancer. In some instances, the subject is diagnosed in having esophagus cancer. In some instances, esophagus cancer further comprises a relapsed or refractory esophagus cancer. In other instances, esophagus cancer comprises a metastatic esophagus cancer. In some cases, the subject is diagnosed in having a relapsed or refractory esophagus cancer. In additional cases, the subject is diagnosed in having a metastatic esophagus cancer.

In some embodiments, an esophagus cancer is any type of esophagus cancer. In some instances, an esophagus cancer comprises esophageal squamous cell carcinoma, esophageal adenocarcinoma, or undifferentiated esophagus cancer.

In some embodiments, the subject diagnosed of having esophagus cancer is further treated with a therapeutic agent. Exemplary therapeutic agents include, but are not limited to, docetaxel, ramucirumab, trastuzumab, or a combination thereof.

In some cases, the subject is diagnosed in having pancreatic cancer. In some instances, pancreatic cancer further comprises a relapsed or refractory pancreatic cancer. In other instances, pancreatic cancer comprises a metastatic pancreatic cancer. In some cases, the subject is diagnosed in having a relapsed or refractory pancreatic cancer. In additional cases, the subject is diagnosed in having a metastatic pancreatic cancer.

In some embodiments, a pancreatic cancer is any type of pancreatic cancer. In some instances, a pancreatic cancer comprises exocrine pancreatic cancers and pancreatic endocrine tumors. In some instances, a pancreatic cancer comprises pancreatic adenocarcinoma, pancreatic adenosquamous carcinomas, pancreatic squamous cell carcinomas, signet ring cell carcinomas, undifferentiated pancreatic carcinomas, undifferentiated pancreatic carcinomas with giant cells, ampullary cancer, gastrinomas, insulinomas, glucagonomas, somatostatinomas, VIPomas, PPomas, or carcinoid tumor.

In some embodiments, the subject diagnosed of having pancreatic cancer is further treated with a therapeutic agent. Exemplary therapeutic agents include, but are not limited to, erlotinib hydrochloride, everolimus, fluorouracil, gemcitabine hydrochloride, irinotecan hydrochloride, lanreotide acetate, mitomycin C, paclitaxel, sunitinib malate, or a combination thereof.

In some cases, the subject is diagnosed in having stomach cancer. In some instances, stomach cancer further comprises a relapsed or refractory stomach cancer. In other instances, stomach cancer comprises a metastatic stomach cancer. In some cases, the subject is diagnosed in having a relapsed or refractory stomach cancer. In additional cases, the subject is diagnosed in having a metastatic stomach cancer.

In some embodiments, a stomach cancer is any type of cancer. In some instances, a stomach cancer comprises gastric adenocarcinoma, lymphoma of the stomach, gastrointestinal stromal tumor, carcinoid tumor, primary squamous cell carcinoma of stomach, gastric small-cell carcinoma, or leiomyo sarcoma of the stomach.

In some embodiments, the subject diagnosed of having stomach cancer is further treated with a therapeutic agent. Exemplary therapeutic agents include, but are not limited to, docetaxel, doxorubicin hydrochloride, fluorouracil, lanreotide acetate, mitomycin C, ramucirumab, trastuzumab, or a combination thereof.

In some embodiments, also described herein include a method of generating a methylation profile of a biomarker. In some instances, the method comprises (a) processing an extracted genomic DNA with a deaminating agent to generate a genomic DNA sample comprising deaminated nucleotides, wherein the extracted genomic DNA is obtained from a biological sample from the subject; (b) detecting a hybridization between the extracted genomic DNA and a probe, wherein the probe hybridizes to cg10673833; and (c) generating a methylation profile based on the detected hybridization between the extracted genomic DNA and the probe.

In some instances, as described elsewhere herein, a pair-wise methylation difference dataset is generated prior to generating a methylation profile. In some cases, the pair-wise methylation difference dataset comprises (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

In some cases, the pair-wise methylation difference dataset is analyzed with a control by a machine learning method to generate a methylation profile. In some cases, the machine learning method utilizes an algorithm selected from one or more of the following: a principal component analysis, a logistic regression analysis, a nearest neighbor analysis, a support vector machine, and a neural network model.

In some embodiments, a probe comprises a DNA probe, RNA probe, or a combination thereof. In some instances, a probe comprises natural nucleic acid molecules and non-natural nucleic acid molecules. In some cases, a probe comprises a labeled probe, such as for example, fluorescently labeled probe or radioactively labeled probe. In some instances, a probe correlates to a CpG site. In some instances, a probe is utilized in a next generation sequencing reaction to generate a CpG methylation data. In further instances, a probe is used in a solution-based next generation sequencing reaction to generate a CpG methylation data. In some cases, a probe comprises a molecular beacon probe, a TaqMan probe, locked nucleic acid probe, a pad-lock probe, or Scorpion probe. In some cases, a probe comprises a pad-lock probe.

In some cases, the method further comprises performing a DNA sequencing reaction such as those described elsewhere herein to quantify the methylation of the biomarker prior to generating a methylation profile.

In some embodiments, a CpG methylation site is located at the promoter region (e.g., induces a promoter methylation). In some instances, promoter methylation leads to a downregulation of its corresponding gene expression. In some instances, one or more CpG methylation sites described supra and in subsequent paragraphs are located at promoter regions, leading to promoter methylation, and subsequent downregulation of the corresponding gene expression. In some instances, the CpG methylation site is as illustrated in Table 1. In some cases, an increase in gene expression leads to a decrease in tumor volume.

In some embodiments, cg10673833 references myosin IG (MYO1G). In some embodiments, described herein is a method of selecting a subject suspected of having a solid tumor for treatment, the method comprises generating a methylation profile comprising myosin IG (MYO1G). In some embodiments, described herein is a method of generating a methylation profile of a gene in a subject in need thereof, comprising detecting a hybridization between the extracted genomic DNA and a probe, wherein the probe hybridizes to myosin IG (MYO1G).

Control

In some embodiments, a control is a methylation value, methylation level, or methylation profile of a sample. In some instances, the control comprises a set of methylation profiles, wherein each said methylation profile is generated from a biological sample obtained from a known cancer type. In some cases, the known cancer type is esophagus cancer, pancreatic cancer, or stomach cancer. In some cases, the known cancer type is a relapsed or refractory esophagus cancer, a relapsed or refractory pancreatic cancer, or a relapsed or refractory stomach cancer. In other cases, the known cancer type is a metastatic esophagus cancer, a metastatic pancreatic cancer, or a metastatic stomach cancer.

In some cases, the known cancer type is esophagus cancer. In some cases, the known cancer type is esophageal squamous cell carcinoma, esophageal adenocarcinoma, or undifferentiated esophagus cancer.

In some cases, the known cancer type is pancreatic cancer. In some cases, the known cancer type is pancreatic adenocarcinoma, pancreatic adenosquamous carcinomas, pancreatic squamous cell carcinomas, signet ring cell carcinomas, undifferentiated pancreatic carcinomas, undifferentiated pancreatic carcinomas with giant cells, ampullary cancer, gastrinomas, insulinomas, glucagonomas, somatostatinomas, VIPomas, PPomas, or carcinoid tumor.

In some cases, the known cancer type is stomach cancer. In some cases, the known cancer type is gastric adenocarcinoma, lymphoma of the stomach, gastrointestinal stromal tumor, carcinoid tumor, primary squamous cell carcinoma of stomach, gastric small-cell carcinoma, or leiomyosarcoma of the stomach.

Probes

In some embodiments, one or more probes described above comprise a structure of Formula I:

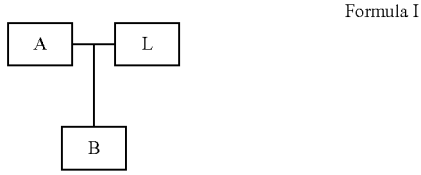

Formula I wherein:
A is a first target-binding region;
B is a second target-binding region; and
L is a linker region;
wherein A comprises at least 70%, 80%, 90%, 95%, or 99% sequence identity to at least 30 contiguous nucleotides starting at position 1 from the 5' terminus of SEQ ID NO: 1; B comprises at least 70%, 80%, 90%, 95%, or 99% sequence identity to at least 12 contiguous nucleotides starting at position 1' from the 3' terminus of the same SEQ ID NO: 1; and wherein L is attached to A; and B is attached to either A or L.

In some instances, L is attached to A and B is attached to L. In some cases, A, B, and L are attached as illustrated in Formula Ia:

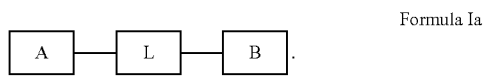

Formula Ia

In some embodiments, A comprises at least 70%, 80%, 90%, 95%, or 99% sequence identity to at least 35 contiguous nucleotides starting at position 1 from the 5' terminus of SEQ ID NO: 1. In some cases, A comprises at least 70%, 80%, 90%, 95%, or 99% sequence identity to at least 40 contiguous nucleotides starting at position 1 from the 5' terminus of SEQ ID NO: 1. In some cases, A comprises at least 70%, 80%, 90%, 95%, or 99% sequence identity to at least 45 contiguous nucleotides starting at position 1 from the 5' terminus of SEQ ID NO: 1. In some cases, A comprises at least 70%, 80%, 90%, 95%, or 99% sequence identity to at least 50 contiguous nucleotides starting at position 1 from the 5' terminus of SEQ ID NO: 1. In some cases, A comprises at least 70%, 80%, 90%, 95%, or 99% sequence identity to at least 55 contiguous nucleotides starting at position 1 from the 5' terminus of SEQ ID NO: 1. In some cases, A comprises at least 70%, 80%, 90%, 95%, or 99% sequence identity to at least 60 contiguous nucleotides starting at position 1 from the 5' terminus of SEQ ID NO: 1. In some cases, A comprises at least 70%, 80%, 90%, 95%, or 99% sequence identity to at least 65 contiguous nucleotides starting at position 1 from the 5' terminus of SEQ ID NO: 1. In some cases, A comprises at least 70%, 80%, 90%, 95%, or 99% sequence identity to at least 70 contiguous nucleotides starting at position 1 from the 5' terminus of SEQ ID NO: 1. In some cases, A comprises at least 70%, 80%, 90%, 95%, or 99% sequence identity to at least 80 contiguous nucleotides starting at position 1 from the 5' terminus of SEQ ID NO: 1. In some cases, A comprises at least 70%, 80%, 90%, 95%, or 99% sequence identity to at least 90 contiguous nucleotides starting at position 1 from the 5' terminus of SEQ ID NO: 1.

In some embodiments, B comprises at least 70%, 80%, 90%, 95%, or 99% sequence identity to at least 14 contiguous nucleotides starting at position 1' from the 3' terminus of the same SEQ ID NO: 1. In some cases, B comprises at least 70%, 80%, 90%, 95%, or 99% sequence identity to at least 15 contiguous nucleotides starting at position 1' from the 3' terminus of the same SEQ ID NO: 1. In some cases, B comprises at least 70%, 80%, 90%, 95%, or 99% sequence identity to at least 18 contiguous nucleotides starting at position 1' from the 3' terminus of the same SEQ ID NO: 1. In some cases, B comprises at least 70%, 80%, 90%, 95%, or 99% sequence identity to at least 20 contiguous nucleotides starting at position 1' from the 3' terminus of the same SEQ ID NO: 1. In some cases, B comprises at least 70%, 80%, 90%, 95%, or 99% sequence identity to at least 22 contiguous nucleotides starting at position 1' from the 3' terminus of the same SEQ ID NO: 1. In some cases, B comprises at least 70%, 80%, 90%, 95%, or 99% sequence identity to at least 25 contiguous nucleotides starting at position 1' from the 3' terminus of the same SEQ ID NO: 1. In some cases, B comprises at least 70%, 80%, 90%, 95%, or 99% sequence identity to at least 28 contiguous nucleotides starting at position 1' from the 3' terminus of the same SEQ ID NO: 1. In some cases, B comprises at least 70%, 80%, 90%, 95%, or 99% sequence identity to at least 30 contiguous nucleotides starting at position 1' from the 3' terminus of the same SEQ ID NO: 1. In some cases, B comprises at least 70%, 80%, 90%, 95%, or 99% sequence identity to at least 35 contiguous nucleotides starting at position 1' from the 3' terminus of the same SEQ ID NO: 1. In some cases, B comprises at least 70%, 80%, 90%, 95%, or 99% sequence identity to at least 40 contiguous nucleotides starting at position 1' from the 3' terminus of the same SEQ ID NO: 1. In some cases, B comprises at least 70%, 80%, 90%, 95%, or 99% sequence identity to at least 45 contiguous nucleotides starting at position 1' from the 3' terminus of the same SEQ ID NO: 1. In some cases, B comprises at least 70%, 80%, 90%, 95%, or 99% sequence identity to at least 50 contiguous nucleotides starting at position 1' from the 3' terminus of the same SEQ ID NO: 1. In some cases, B comprises at least 70%, 80%, 90%, 95%, or 99% sequence identity to at least 55 contiguous nucleotides starting at position 1' from the 3' terminus of the same SEQ ID NO: 1. In some cases, B comprises at least 70%, 80%, 90%, 95%, or 99% sequence identity to at least 60 contiguous nucleotides starting at position 1' from the 3' terminus of the same SEQ ID NO: 1. In some cases, B comprises at least 70%, 80%, 90%, 95%, or 99% sequence identity to at least 65 contiguous nucleotides starting at position 1' from the 3' terminus of the same SEQ ID NO: 1. In some cases, B comprises at least 70%, 80%, 90%, 95%, or 99% sequence identity to at least 70 contiguous nucleotides starting at position 1' from the 3' terminus of the same SEQ ID NO: 1. In some cases, B comprises at least 70%, 80%, 90%, 95%, or 99% sequence identity to at least 80 contiguous nucleotides starting at position 1' from the 3' terminus of the same SEQ ID NO: 1. In some cases, B comprises at least 70%, 80%, 90%, 95%, or 99% sequence identity to at least 90 contiguous nucleotides starting at position 1' from the 3' terminus of the same SEQ ID NO: 1.

In some instances, a probe described above is used in a next generation sequencing reaction to generate a CpG methylation data. In some instances, the probe is used in a solution-based next generation sequencing reaction to generate a CpG methylation data. In some instances, the next generation sequencing reaction comprises 454 Life Sciences platform (Roche, Branford, Conn.); lllumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.); QX200™ Droplet Digital™ PCR System from Bio-Rad; DNA Sequencing by Ligation, SOLiD System (Applied Biosystems/Life Technologies); the Helicos True Single Molecule DNA sequencing technology; semiconductor sequencing (Ion Torrent; Personal Genome Machine); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g., Oxford Nanopore, Genia Technologies, and Nabsys). In some instances, the solution-based next generation sequencing reaction is a droplet digital PCR sequencing method.

In some instances, each probe correlates to a CpG site. In some instances, each probe correlates to a biomarker (e.g., CpG site) as illustrated in Table 5.

In some instances, L is between 10 and 60, 15 and 55, 20 and 50, 25 and 45, and 30 and 40 nucleotides in length. In some instances, L is about 15, 20, 25, 30, 35, 40, 45, 50, 55, or 60 nucleotides in length.

In some instances, L further comprises an adaptor region. In some instances, the adaptor region comprises a sequence used to identify each probe. In some instances as illustrated in Table 5, the adaptor region in each illustrative sequence is reflected by a series of N, in which each N is A, T, G, or C.

In some embodiments, a probe described herein comprises at least 50%, 60%, 70%, 80%, 85%, 90%, 91%, 92%, 93%, 94%, 95%, 96%, 97%, 98%, or 99% sequence identity to SEQ ID NO: 1. In some instances, the probe comprises at least 50% sequence identity to SEQ ID NO: 1. In some instances, the probe comprises at least 60% sequence identity to SEQ ID NO: 1. In some instances, the probe comprises at least 70% sequence identity to SEQ ID NO: 1. In some instances, the probe comprises at least 80% sequence identity to SEQ ID NO: 1. In some instances, the probe comprises at least 85% sequence identity to SEQ ID NO: 1. In some instances, the probe comprises at least 90% sequence identity to SEQ ID NO: 1. In some instances, the probe comprises at least 91% sequence identity to SEQ ID NO: 1. In some instances, the probe comprises at least 92% sequence identity to SEQ ID NO: 1. In some instances, the probe comprises at least 93% sequence identity to SEQ ID NO: 1. In some instances, the probe comprises at least 94% sequence identity to SEQ ID NO: 1. In some instances, the probe comprises at least 95% sequence identity to SEQ ID NO: 1. In some instances, the probe comprises at least 96% sequence identity to SEQ ID NO: 1. In some instances, the probe comprises at least 97% sequence identity to SEQ ID NO: 1. In some instances, the probe comprises at least 98% sequence identity to SEQ ID NO: 1. In some instances, the probe comprises at least 99% sequence identity to SEQ ID NO: 1. In some instances, the probe comprises 100% sequence identity to SEQ ID NO: 1. In some instances, the probe consists of SEQ ID NO: 1.

In some cases, a probe described above is utilized in a digital PCR sequencing method. In some cases, the probe is utilized in a droplet digital PCR (ddPCR) sequencing method.

Detection Methods

In some embodiments, a number of methods are utilized to measure, detect, determine, identify, and characterize the methylation status/level of a gene or a biomarker (e.g., CpG island-containing region/fragment) in identifying a subject as having esophagus cancer, pancreatic cancer, or stomach cancer, or differentiate between esophagus cancer, pancreatic cancer, or stomach cancer types.

In some instances, the methylation profile is generated from a biological sample isolated from an individual. In some embodiments, the biological sample is a biopsy. In some instances, the biological sample is a tissue sample. In some instances, the biological sample is a tissue biopsy sample. In some instances, the biological sample is a blood sample. In other instances, the biological sample is a cell-free biological sample. In other instances, the biological sample is a circulating tumor DNA sample. In one embodiment, the biological sample is a cell free biological sample containing circulating tumor DNA.

In some embodiments, a biomarker (or an epigenetic marker) is obtained from a liquid sample. In some embodiments, the liquid sample comprises blood and other liquid samples of biological origin (including, but not limited to, peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood. In some embodiments, the biological fluid is blood, a blood derivative or a blood fraction, e.g., serum or plasma. In a specific embodiment, a sample comprises a blood sample. In another embodiment, a serum sample is used. In another embodiment, a sample comprises urine. In some embodiments, the liquid sample also encompasses a sample that has been manipulated in any way after their procurement, such as by centrifugation, filtration, precipitation, dialysis, chromatography, treatment with reagents, washed, or enriched for certain cell populations.

In some embodiments, a biomarker (or an epigenetic marker) is obtained from a tissue sample. In some instances, a tissue corresponds to any cell(s). Different types of tissue correspond to different types of cells (e.g., liver, lung, blood, connective tissue, and the like), but also healthy cells vs. tumor cells or to tumor cells at various stages of neoplasia, or to displaced malignant tumor cells. In some embodiments, a tissue sample further encompasses a clinical sample, and also includes cells in culture, cell supernatants, organs, and the like. Samples also comprise fresh-frozen and/or formalin-fixed, paraffin-embedded tissue blocks, such as blocks prepared from clinical or pathological biopsies, prepared for pathological analysis or study by immunohistochemistry.

In some embodiments, a biomarker (or an epigenetic marker) is methylated or unmethylated in a normal sample (e.g., normal or control tissue without disease, or normal or control body fluid, stool, blood, serum, amniotic fluid), most importantly in healthy stool, blood, serum, amniotic fluid or other body fluid. In other embodiments, a biomarker (or an epigenetic marker) is hypomethylated or hypermethylated in a sample from a patient having or at risk of a disease (e.g., one or more indications described herein); for example, at a decreased or increased (respectively) methylation frequency of at least about 50%, at least about 60%, at least about 70%, at least about 75%, at least about 80%, at least about 85%, at least about 90%, at least about 95%, or about 100% in comparison to a normal sample. In one embodiment, a sample is also hypomethylated or hypermethylated in comparison to a previously obtained sample analysis of the same patient having or at risk of a disease (e.g., one or more indications described herein), particularly to compare progression of a disease.

In some embodiments, a methylome comprises a set of epigenetic markers or biomarkers, such as a biomarker described above. In some instances, a methylome that corresponds to the methylome of a tumor of an organism (e.g., a human) is classified as a tumor methylome. In some cases, a tumor methylome is determined using tumor tissue or cell-free (or protein-free) tumor DNA in a biological sample. Other examples of methylomes of interest include the methylomes of organs that contribute DNA into a bodily fluid (e.g. methylomes of tissue such as brain, breast, lung, the prostate, and the kidneys, plasma, etc.).

In some embodiments, a plasma methylome is the methylome determined from the plasma or serum of an animal (e.g., a human). In some instances, the plasma methylome is an example of a cell-free or protein-free methylome since plasma and serum include cell-free DNA. The plasma methylome is also an example of a mixed methylome since it is a mixture of tumor and other methylomes of interest. In some instances, the urine methylome is determined from the urine sample of a subject. In some cases, a cellular methylome corresponds to the methylome determined from cells (e.g., blood cells) of the patient. The methylome of the blood cells is called the blood cell methylome (or blood methylome).

In some embodiments, DNA (e.g., genomic DNA such as extracted genomic DNA or treated genomic DNA) is isolated by any means standard in the art, including the use of commercially available kits. Briefly, wherein the DNA of interest is encapsulated in by a cellular membrane the biological sample is disrupted and lysed by enzymatic, chemical or mechanical means. In some cases, the DNA solution is then cleared of proteins and other contaminants e.g. by digestion with proteinase K. The DNA is then recovered from the solution. In such cases, this is carried out by means of a variety of methods including salting out, organic extraction or binding of the DNA to a solid phase support. In some instances, the choice of method is affected by several factors including time, expense and required quantity of DNA.

Wherein the sample DNA is not enclosed in a membrane (e.g. circulating DNA from a cell free sample such as blood or urine) methods standard in the art for the isolation and/or purification of DNA are optionally employed (See, for example, Bettegowda et al. Detection of Circulating Tumor DNA in Early- and Late-Stage Human Malignancies. Sci. Transl. Med, 6(224): ra24. 2014). Such methods include the use of a protein degenerating reagent e.g. chaotropic salt e.g. guanidine hydrochloride or urea; or a detergent e.g. sodium dodecyl sulphate (SDS), cyanogen bromide. Alternative methods include but are not limited to ethanol precipitation or propanol precipitation, vacuum concentration amongst others by means of a centrifuge. In some cases, the person skilled in the art also make use of devices such as filter devices e.g. ultrafiltration, silica surfaces or membranes, magnetic particles, polystyrol particles, polystyrol surfaces, positively charged surfaces, and positively charged membranes, charged membranes, charged surfaces, charged switch membranes, charged switched surfaces.

In some instances, once the nucleic acids have been extracted, methylation analysis is carried out by any means known in the art. A variety of methylation analysis procedures are known in the art and may be used to practice the methods disclosed herein. These assays allow for determination of the methylation state of one or a plurality of CpG sites within a tissue sample. In addition, these methods may be used for absolute or relative quantification of methylated nucleic acids. Such methylation assays involve, among other techniques, two major steps. The first step is a methylation specific reaction or separation, such as (i) bisulfite treatment, (ii) methylation specific binding, or (iii) methylation specific restriction enzymes. The second major step involves (i) amplification and detection, or (ii) direct detection, by a variety of methods such as (a) PCR (sequence-specific amplification) such as Taqman®, (b) DNA sequencing of untreated and bisulfite-treated DNA, (c) sequencing by ligation of dye-modified probes (including cyclic ligation and cleavage), (d) pyrosequencing, (e) single-molecule sequencing, (f) mass spectroscopy, or (g) Southern blot analysis.

Additionally, restriction enzyme digestion of PCR products amplified from bisulfite-converted DNA may be used, e.g., the method described by Sadri and Hornsby (1996, Nucl. Acids Res. 24:5058-5059), or COBRA (Combined Bisulfite Restriction Analysis) (Xiong and Laird, 1997, Nucleic Acids Res. 25:2532-2534). COBRA analysis is a quantitative methylation assay useful for determining DNA methylation levels at specific gene loci in small amounts of genomic DNA. Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Frommer et al, 1992, Proc. Nat. Acad. Sci. USA, 89, 1827-1831). PCR amplification of the bisulfite converted DNA is then performed using primers specific for the CpG sites of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from micro-dissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfo nation buffer; DNA recovery reagents or kits (e.g., precipitation, ultrafiltration, affinity column); desulfonation buffer; and DNA recovery components.

In an embodiment, the methylation profile of selected CpG sites is determined using methylation-Specific PCR (MSP). MSP allows for assessing the methylation status of virtually any group of CpG sites within a CpG island, independent of the use of methylation-sensitive restriction enzymes (Herman et al, 1996, Proc. Nat. Acad. Sci. USA, 93, 9821-9826; U.S. Pat. Nos. 5,786,146, 6,017,704, 6,200,756, 6,265,171 (Herman and Baylin); U.S. Pat. Pub. No. 2010/0144836 (Van Engeland et al)). Briefly, DNA is modified by a deaminating agent such as sodium bisulfite to convert unmethylated, but not methylated cytosines to uracil, and subsequently amplified with primers specific for methylated versus unmethylated DNA. In some instances, typical reagents (e.g., as might be found in a typical MSP-based kit) for MSP analysis include, but are not limited to: methylated and unmethylated PCR primers for specific gene (or methylation-altered DNA sequence or CpG island), optimized PCR buffers and deoxynucleotides, and specific probes. In some instances, a quantitative multiplexed methylation specific PCR (QM-PCR) as described by Fackler et al. Fackler et al, 2004, Cancer Res. 64(13) 4442-4452; or Fackler et al, 2006, Clin. Cancer Res. 12(11 Pt 1) 3306-3310, is used.

In an embodiment, the methylation profile of selected CpG sites is determined using MethyLight and/or Heavy Methyl Methods. The MethyLight and Heavy Methyl assays are a high-throughput quantitative methylation assay that utilizes fluorescence-based real-time PCR (Taq Man®) technology that requires no further manipulations after the PCR step (Eads, C. A. et al, 2000, Nucleic Acid Res. 28, e 32; Cottrell et al, 2007, J. Urology 177, 1753, U.S. Pat. No. 6,331,393 (Laird et al)). Briefly, the MethyLight process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. In some cases, sequence discrimination occurs either at the level of the amplification process or at the level of the fluorescence detection process, or both. In some cases, the MethyLight assay is used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites. Typical reagents (e.g., as might be found in a typical MethyLight-based kit) for MethyLight analysis may include, but are not limited to: PCR primers for specific gene (or methylation-altered DNA sequence or CpG island); TaqMan® probes; optimized PCR buffers and deoxynucleotides; and Taq polymerase.

Quantitative MethyLight uses bisulfite to convert genomic DNA and the methylated sites are amplified using PCR with methylation independent primers. Detection probes specific for the methylated and unmethylated sites with two different fluorophores provides simultaneous quantitative measurement of the methylation. The Heavy Methyl technique begins with bisulfate conversion of DNA. Next specific blockers prevent the amplification of unmethylated DNA. Methylated genomic DNA does not bind the blockers and their sequences will be amplified. The amplified sequences are detected with a methylation specific probe. (Cottrell et al, 2004, Nuc. Acids Res. 32:e10).

The Ms-SNuPE technique is a quantitative method for assessing methylation differences at specific CpG sites based on bisulfite treatment of DNA, followed by single-nucleotide primer extension (Gonzalgo and Jones, 1997, Nucleic Acids Res. 25, 2529-2531). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. In some cases, small amounts of DNA are analyzed (e.g., microdissected pathology sections), and the method avoids utilization of restriction enzymes for determining the methylation status at CpG sites. Typical reagents (e.g., as is found in a typical Ms-SNuPE-based kit) for Ms-SNuPE analysis include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In another embodiment, the methylation status of selected CpG sites is determined using differential Binding-based Methylation Detection Methods. For identification of differentially methylated regions, one approach is to capture methylated DNA. This approach uses a protein, in which the methyl binding domain of MBD2 is fused to the Fc fragment of an antibody (MBD-FC) (Gebhard et al, 2006, Cancer Res. 66:6118-6128; and PCT Pub. No. WO 2006/056480 A2 (Relhi)). This fusion protein has several advantages over conventional methylation specific antibodies. The MBD FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC, on the other hand, binds DNA molecules regardless of their methylation status. The strength of this protein—DNA interaction is defined by the level of DNA methylation. After binding genomic DNA, eluate solutions of increasing salt concentrations can be used to fractionate non-methylated and methylated DNA allowing for a more controlled separation (Gebhard et al, 2006, Nucleic Acids Res. 34: e82). Consequently this method, called Methyl-CpG immunoprecipitation (MCIP), not only enriches, but also fractionates genomic DNA according to methylation level, which is particularly helpful when the unmethylated DNA fraction should be investigated as well.

In an alternative embodiment, a 5-methyl cytidine antibody to bind and precipitate methylated DNA. Antibodies are available from Abcam (Cambridge, Mass.), Diagenode (Sparta, N.J.) or Eurogentec (c/o AnaSpec, Fremont, Calif.). Once the methylated fragments have been separated they may be sequenced using microarray based techniques such as methylated CpG-island recovery assay (MIRA) or methylated DNA immunoprecipitation (MeDIP) (Pelizzola et al, 2008, Genome Res. 18, 1652-1659; O'Geen et al, 2006, BioTechniques 41(5), 577-580, Weber et al, 2005, Nat. Genet. 37, 853-862; Horak and Snyder, 2002, Methods Enzymol, 350, 469-83; Lieb, 2003, Methods Mol Biol, 224, 99-109). Another technique is methyl-CpG binding domain column/segregation of partly melted molecules (MBD/SPM, Shiraishi et al, 1999, Proc. Natl. Acad. Sci. USA 96(6):2913-2918).

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 7,901,880; and 7,459,274. In some embodiments, amplification can be performed using primers that are gene specific.

For example, there are methyl-sensitive enzymes that preferentially or substantially cleave or digest at their DNA recognition sequence if it is non-methylated. Thus, an unmethylated DNA sample is cut into smaller fragments than a methylated DNA sample. Similarly, a hypermethylated DNA sample is not cleaved. In contrast, there are methyl-sensitive enzymes that cleave at their DNA recognition sequence only if it is methylated. Methyl-sensitive enzymes that digest unmethylated DNA suitable for use in methods of the technology include, but are not limited to, HpaII, HhaI, MaeII, BstUI and AciI. In some instances, an enzyme that is used is HpaII that cuts only the unmethylated sequence CCGG. In other instances, another enzyme that is used is HhaI that cuts only the unmethylated sequence GCGC. Both enzymes are available from New England BioLabs®, Inc. Combinations of two or more methyl-sensitive enzymes that digest only unmethylated DNA are also used. Suitable enzymes that digest only methylated DNA include, but are not limited to, DpnI, which only cuts at fully methylated 5'-GATC sequences, and McrBC, an endonuclease, which cuts DNA containing modified cytosines (5-methylcytosine or 5-hydroxymethylcytosine or N4-methylcytosine) and cuts at recognition site 5' . . . PumC(N4o-3ooo) PumC . . . 3' (New England BioLabs, Inc., Beverly, Mass.). Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al. Molecular Biology: A Laboratory Approach, Cold Spring Harbor, N.Y. 1989) provide a general description of methods for using restriction enzymes and other enzymes.

In some instances, a methylation-dependent restriction enzyme is a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McRBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use with one or more methods described herein.

In some cases, a methylation-sensitive restriction enzyme is a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al, 22(17) NUCLEIC ACIDS RES. 3640-59 (1994). Suitable methylation-sensitive restriction enzymes that do not cleave DNA at or near their recognition sequence when a cytosine within the recognition sequence is methylated at position C5 include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinPl I, HinC II, Hpa II, Hpy99 I, HpyCH4 IV, Kas I, Mbo I, Mlu I, MapAl I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position N6 include, e.g., Mbo I. One of skill in the art will appreciate that any methylation-sensitive restriction enzyme, including homologs and orthologs of the restriction enzymes described herein, is also suitable for use with one or more of the methods described herein. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

In alternative embodiments, adaptors are optionally added to the ends of the randomly fragmented DNA, the DNA is then digested with a methylation-dependent or methylation-sensitive restriction enzyme, and intact DNA is subsequently amplified using primers that hybridize to the adaptor sequences. In this case, a second step is performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

In some instances, the quantity of methylation of a locus of DNA is determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

The methylated CpG island amplification (MCA) technique is a method that can be used to screen for altered methylation patterns in genomic DNA, and to isolate specific sequences associated with these changes (Toyota et al, 1999, Cancer Res. 59, 2307-2312, U.S. Pat. No. 7,700,324 (Issa et al)). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Additional methylation detection methods include those methods described in, e.g., U.S. Pat. Nos. 7,553,627; 6,331, 393; U.S. patent Ser. No. 12/476,981; U.S. Patent Publication No. 2005/0069879; Rein, et al, 26(10) NUCLEIC ACIDS RES. 2255-64 (1998); and Olek et al, 17(3) NAT. GENET. 275-6 (1997).

In another embodiment, the methylation status of selected CpG sites is determined using Methylation-Sensitive High Resolution Melting (HRM). Recently, Wojdacz et al. reported methylation-sensitive high resolution melting as a technique to assess methylation. (Wojdacz and Dobrovic, 2007, Nuc. Acids Res. 35(6) e41; Wojdacz et al. 2008, Nat. Prot. 3(12) 1903-1908; Balic et al, 2009 J. Mol. Diagn. 11 102-108; and US Pat. Pub. No. 2009/0155791 (Wojdacz et al)). A variety of commercially available real time PCR machines have HRM systems including the Roche LightCycler480, Corbett Research RotorGene6000, and the Applied Biosystems 7500. HRM may also be combined with other amplification techniques such as pyrosequencing as described by Candiloro et al. (Candiloro et al, 2011, Epigenetics 6(4) 500-507).

In another embodiment, the methylation status of selected CpG locus is determined using a primer extension assay, including an optimized PCR amplification reaction that produces amplified targets for analysis using mass spectrometry. The assay can also be done in multiplex. Mass spectrometry is a particularly effective method for the detection of polynucleotides associated with the differentially methylated regulatory elements. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. This method is described in detail in PCT Pub. No. WO 2005/012578A1 (Beaulieu et al), which is hereby incorporated by reference in its entirety. For methylation analysis, the assay can be adopted to detect bisulfite introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Other methods for DNA methylation analysis include restriction landmark genomic scanning (RLGS, Costello et al, 2002, Meth. Mol Biol, 200, 53-70), methylation-sensitive-representational difference analysis (MS-RDA, Ushijima and Yamashita, 2009, Methods Mol Biol 507, 1 17-130). Comprehensive high-throughput arrays for relative methylation (CHARM) techniques are described in WO 2009/021141 (Feinberg and Irizarry). The Roche® NimbleGen® microarrays including the Chromatin Immunoprecipitation-on-chip (ChIP-chip) or methylated DNA immunoprecipitation-on-chip (MeDIP-chip). These tools have been used for a variety of cancer applications including melanoma, liver cancer and lung cancer (Koga et al, 2009, Genome Res., 19, 1462-1470; Acevedo et al, 2008, Cancer Res., 68, 2641-2651; Rauch et al, 2008, Proc. Nat. Acad. Sci. USA, 105, 252-257). Others have reported bisulfate conversion, padlock probe hybridization, circularization, amplification and next generation or multiplexed sequencing for high throughput detection of methylation (Deng et al, 2009, Nat. Biotechnol 27, 353-360; Ball et al, 2009, Nat. Biotechnol 27, 361-368; U.S. Pat. No. 7,611,869 (Fan)). As an alternative to bisulfate oxidation, Bayeyt et al. have reported selective oxidants that oxidize 5-methylcytosine, without reacting with thymidine, which are followed by PCR or pyro sequencing (WO 2009/049916 (Bayeyt et al).

In some instances, quantitative amplification methods (e.g., quantitative PCR or quantitative linear amplification) are used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., DeGraves, et al, 34(1) BIOTECHNIQUES 106-15 (2003); Deiman B, et al., 20(2) MOL. BIOTECHNOL. 163-79 (2002); and Gibson et al, 6 GENOME RESEARCH 995-1001 (1996).

Following reaction or separation of nucleic acid in a methylation specific manner, the nucleic acid in some cases are subjected to sequence-based analysis. For example, once it is determined that one particular genomic sequence from a sample is hypermethylated or hypomethylated compared to its counterpart, the amount of this genomic sequence can be determined. Subsequently, this amount can be compared to a standard control value and used to determine the present of esophagus cancer, pancreatic cancer, or stomach cancer in the sample. In many instances, it is desirable to amplify a nucleic acid sequence using any of several nucleic acid amplification procedures which are well known in the art. Specifically, nucleic acid amplification is the chemical or enzymatic synthesis of nucleic acid copies which contain a sequence that is complementary to a nucleic acid sequence being amplified (template). The methods and kits may use any nucleic acid amplification or detection methods known to one skilled in the art, such as those described in U.S. Pat. No. 5,525,462 (Takarada et al); U.S. Pat. No. 6,114,117 (Hepp et al); U.S. Pat. No. 6,127,120 (Graham et al); U.S. Pat. No. 6,344,317 (Urnovitz); U.S. Pat. No. 6,448,001 (Oku); U.S. Pat. No. 6,528,632 (Catanzariti et al); and PCT Pub. No. WO 2005/111209 (Nakajima et al).

In some embodiments, the nucleic acids are amplified by PCR amplification using methodologies known to one skilled in the art. One skilled in the art will recognize, however, that amplification can be accomplished by any known method, such as ligase chain reaction (LCR), Q-replicas amplification, rolling circle amplification, transcription amplification, self-sustained sequence replication, nucleic acid sequence-based amplification (NASBA), each of which provides sufficient amplification. Branched-DNA technology is also optionally used to qualitatively demonstrate the presence of a sequence of the technology, which represents a particular methylation pattern, or to quantitatively determine the amount of this particular genomic sequence in a sample. Nolte reviews branched-DNA signal amplification for direct quantitation of nucleic acid sequences in clinical samples (Nolte, 1998, Adv. Clin. Chem. 33:201-235).

The PCR process is well known in the art and include, for example, reverse transcription PCR, ligation mediated PCR, digital PCR (dPCR), or droplet digital PCR (ddPCR). For a review of PCR methods and protocols, see, e.g., Innis et al, eds., PCR Protocols, A Guide to Methods and Application, Academic Press, Inc., San Diego, Calif. 1990; U.S. Pat. No. 4,683,202 (Mullis). PCR reagents and protocols are also available from commercial vendors, such as Roche Molecular Systems. In some instances, PCR is carried out as an automated process with a thermostable enzyme. In this process, the temperature of the reaction mixture is cycled through a denaturing region, a primer annealing region, and an extension reaction region automatically. Machines specifically adapted for this purpose are commercially available.

In some embodiments, amplified sequences are also measured using invasive cleavage reactions such as the Invader® technology (Zou et al, 2010, Association of Clinical Chemistry (AACC) poster presentation on Jul. 28, 2010, "Sensitive Quantification of Methylated Markers with a Novel Methylation Specific Technology; and U.S. Pat. No. 7,011,944 (Prudent et al)).

Suitable next generation sequencing technologies are widely available. Examples include the 454 Life Sciences platform (Roche, Branford, Conn.) (Margulies et al. 2005 Nature, 437, 376-380); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al, 2006, Genome Res. 16, 383-393; U.S. Pat. Nos. 6,306,597 and 7,598,035 (Macevicz); U.S. Pat. No. 7,232,656 (Balasubramanian et al.)); QX200™ Droplet Digital™ PCR System from Bio-Rad; or DNA Sequencing by Ligation, SOLiD System (Applied Bio systems/Life Technologies; U.S. Pat. Nos. 6,797,470, 7,083,917, 7,166,434, 7,320,865, 7,332,285, 7,364,858, and 7,429,453 (Barany et al); the Helicos True Single Molecule DNA sequencing technology (Harris et al, 2008 Science, 320, 106-109; U.S. Pat. Nos. 7,037,687 and 7,645,596 (Williams et al); U.S. Pat. No. 7,169,560 (Lapidus et al); U.S. Pat. No. 7,769,400 (Harris)), the single molecule, real-time (SMRT™) technology of Pacific Biosciences, and sequencing (Soni and Meller, 2007, Clin. Chem. 53, 1996-2001); semiconductor sequencing (Ion Torrent; Personal Genome Machine); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g., Oxford Nanopore, Genia Technologies, and Nabsys). These systems allow the sequencing of many nucleic acid molecules isolated from a specimen at high orders of multiplexing in a parallel fashion. Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. Machines for pyrosequencing and methylation specific reagents are available from Qiagen, Inc. (Valencia, Calif.). See also Tost and Gut, 2007, Nat. Prot. 2 2265-2275. An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support;

and sequencing amplified nucleotide sequences by pyrosequencing methodology (e.g., Nakano et al, 2003, J. Biotech. 102, 117-124). Such a system can be used to exponentially amplify amplification products generated by a process described herein, e.g., by ligating a heterologous nucleic acid to the first amplification product generated by a process described herein.

CpG Methylation Data Analysis Methods

In certain embodiments, the methylation values measured for biomarkers of a biomarker panel are mathematically combined and the combined value is correlated to the underlying diagnostic question. In some instances, methylated biomarker values are combined by any appropriate state of the art mathematical method. Well-known mathematical methods for correlating a biomarker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate an epigenetic marker or biomarker combination described herein. In one embodiment, the method used in a correlating methylation status of an epigenetic marker or biomarker combination, e.g. to diagnose esophagus cancer, pancreatic cancer, or stomach cancer, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. O., Pattern Classification, Wiley Interscience, 2nd Edition (2001).

In one embodiment, the correlated results for each methylation panel are rated by their correlation to the disease or tumor type positive state, such as for example, by p-value test or t-value test or F-test. Rated (best first, i.e. low p- or t-value) biomarkers are then subsequently selected and added to the methylation panel until a certain diagnostic value is reached. Such methods include identification of methylation panels, or more broadly, genes that were differentially methylated among several classes using, for example, a random-variance t-test (Wright G. W. and Simon R, Bioinformatics 19:2448-2455, 2003). Other methods include the step of specifying a significance level to be used for determining the epigenetic markers that will be included in the biomarker panel. Epigenetic markers that are differentially methylated between the classes at a univariate parametric significance level less than the specified threshold are included in the panel. It doesn't matter whether the specified significance level is small enough to exclude enough false discoveries. In some problems better prediction is achieved by being more liberal about the biomarker panels used as features. In some cases, the panels are biologically interpretable and clinically applicable, however, if fewer markers are included. Similar to cross-validation, biomarker selection is repeated for each training set created in the cross-validation process. That is for the purpose of providing an unbiased estimate of prediction error. The methylation panel for use with new patient sample data is the one resulting from application of the methylation selection and classifier of the "known" methylation information, or control methylation panel.

Models for utilizing methylation profile to predict the class of future samples can also be used. These models may be based on the Compound Covariate Predictor (Radmacher et al. Journal of Computational Biology 9:505-511, 2002), Diagonal Linear Discriminant Analysis (Dudoit et al. Journal of the American Statistical Association 97:77-87, 2002), Nearest Neighbor Classification (also Dudoit et al.), and Support Vector Machines with linear kernel (Ramaswamy et al. PNAS USA 98:15149-54, 2001). The models incorporated markers that were differentially methylated at a given significance level (e.g. 0.01, 0.05 or 0.1) as assessed by the random variance t-test (Wright G. W. and Simon R. Bioinformatics 19:2448-2455, 2003). The prediction error of each model using cross validation, preferably leave-one-out cross-validation (Simon et al. Journal of the National Cancer Institute 95:14-18, 2003 can be estimated. For each leave-one-out cross-validation training set, the entire model building process is repeated, including the epigenetic marker selection process. In some instances, it is also evaluated in whether the cross-validated error rate estimate for a model is significantly less than one would expect from random prediction. In some cases, the class labels are randomly permuted and the entire leave-one-out cross-validation process is then repeated. The significance level is the proportion of the random permutations that gives a cross-validated error rate no greater than the cross-validated error rate obtained with the real methylation data.

Another classification method is the greedy-pairs method described by Bo and Jonassen (Genome Biology 3(4): research0017.1-0017.11, 2002). The greedy-pairs approach starts with ranking all markers based on their individual t-scores on the training set. This method attempts to select pairs of markers that work well together to discriminate the classes.

Furthermore, a binary tree classifier for utilizing methylation profile is optionally used to predict the class of future samples. The first node of the tree incorporated a binary classifier that distinguished two subsets of the total set of classes. The individual binary classifiers are based on the "Support Vector Machines" incorporating markers that were differentially expressed among markers at the significance level (e.g. 0.01, 0.05 or 0.1) as assessed by the random variance t-test (Wright G. W. and Simon R. Bioinformatics 19:2448-2455, 2003). Classifiers for all possible binary partitions are evaluated and the partition selected is that for which the cross-validated prediction error is minimum. The process is then repeated successively for the two subsets of classes determined by the previous binary split. The prediction error of the binary tree classifier can be estimated by cross-validating the entire tree building process. This overall cross-validation includes re-selection of the optimal partitions at each node and re-selection of the markers used for each cross-validated training set as described by Simon et al. (Simon et al. Journal of the National Cancer Institute 95:14-18, 2003). Several-fold cross validation in which a fraction of the samples is withheld, a binary tree developed on the remaining samples, and then class membership is predicted for the samples withheld. This is repeated several times, each time withholding a different percentage of the samples. The samples are randomly partitioned into fractional test sets (Simon R and Lam A. BRB-ArrayTools User Guide, version 3.2. Biometric Research Branch, National Cancer Institute).

Thus, in one embodiment, the correlated results for each marker b) are rated by their correct correlation to the disease, preferably by p-value test. It is also possible to include a step in that the markers are selected d) in order of their rating.

In additional embodiments, factors such as the value, level, feature, characteristic, property, etc. of a transcription rate, mRNA level, translation rate, protein level, biological activity, cellular characteristic or property, genotype, phenotype, etc. can be utilized in addition prior to, during, or after administering a therapy to a patient to enable further analysis of the patient's cancer status.

In some embodiments, a diagnostic test to correctly predict status is measured as the sensitivity of the assay, the specificity of the assay or the area under a receiver operated characteristic ("ROC") curve. In some instances, sensitivity is the percentage of true positives that are predicted by a test to be positive, while specificity is the percentage of true negatives that are predicted by a test to be negative. In some cases, an ROC curve provides the sensitivity of a test as a function of 1-specificity. The greater the area under the ROC curve, for example, the more accurate or powerful the predictive value of the test. Other useful measures of the utility of a test include positive predictive value and negative predictive value. Positive predictive value is the percentage of people who test positive that are actually positive. Negative predictive value is the percentage of people who test negative that are actually negative.

In some embodiments, one or more of the biomarkers disclosed herein show a statistical difference in different samples of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9. In some instances, the biomarkers are differentially methylated in different subjects with or without esophagus cancer, pancreatic cancer, or stomach cancer. In additional instances, the biomarkers for different subtypes of esophagus cancer, pancreatic cancer, or stomach cancer are differentially methylated. In certain embodiments, the biomarkers are measured in a patient sample using the methods described herein and compared, for example, to predefined biomarker levels and are used to determine whether the patient has esophagus cancer, pancreatic cancer, or stomach cancer, and/or which esophagus cancer, pancreatic cancer, or stomach cancer subtype does the patient have. In other embodiments, the correlation of a combination of biomarkers in a patient sample is compared, for example, to a predefined set of biomarkers. In some embodiments, the measurement(s) is then compared with a relevant diagnostic amount(s), cut-off(s), or multivariate model scores that distinguish between the presence or absence of esophagus cancer, pancreatic cancer, or stomach cancer, or between esophagus cancer, pancreatic cancer, or stomach cancer subtypes. As is well understood in the art, by adjusting the particular diagnostic cut-off(s) used in an assay, one can increase sensitivity or specificity of the diagnostic assay depending on the preference of the diagnostician. In some embodiments, the particular diagnostic cut-off is determined, for example, by measuring the amount of biomarker hypermethylation or hypomethylation in a statistically significant number of samples from patients with or without esophagus cancer, pancreatic cancer, or stomach cancer and from patients with different esophagus cancer, pancreatic cancer, or stomach cancer subtypes, and drawing the cut-off to suit the desired levels of specificity and sensitivity.

Kits/Article of Manufacture

In some embodiments, provided herein include kits for detecting and/or characterizing the methylation profile of a biomarker described herein. In some instances, the kit comprises a plurality of primers or probes to detect or measure the methylation status/levels of one or more samples. Such kits comprise, in some instances, at least one polynucleotide that hybridizes to at least one of the methylation marker sequences described herein and at least one reagent for detection of gene methylation. Reagents for detection of methylation include, e.g., sodium bisulfate, polynucleotides designed to hybridize to sequence that is the product of a marker sequence if the marker sequence is not methylated (e.g., containing at least one C-U conversion), and/or a methylation-sensitive or methylation-dependent restriction enzyme. In some cases, the kits provide solid supports in the form of an assay apparatus that is adapted to use in the assay. In some instances, the kits further comprise detectable labels, optionally linked to a polynucleotide, e.g., a probe, in the kit.

In some embodiments, the kits comprise one or more (e.g., 1, 2, 3, 4, or more) different polynucleotides (e.g., primers and/or probes) capable of specifically amplifying at least a portion of a DNA region of a biomarker described herein. Optionally, one or more detectably-labeled polypeptides capable of hybridizing to the amplified portion are also included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of an epigenetic marker described herein.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region of an epigenetic marker described herein.

In some embodiments, the kits comprise a methylation binding moiety and one or more polynucleotides to quantify the number of copies of at least a portion of a DNA region of a marker described herein. A methylation binding moiety refers to a molecule (e.g., a polypeptide) that specifically binds to methyl-cytosine.

Examples include restriction enzymes or fragments thereof that lack DNA cutting activity but retain the ability to bind methylated DNA, antibodies that specifically bind to methylated DNA, etc.).

In some embodiments, the kit includes a packaging material. As used herein, the term "packaging material" can refer to a physical structure housing the components of the kit. In some instances, the packaging material maintains sterility of the kit components, and is made of material commonly used for such purposes (e.g., paper, corrugated fiber, glass, plastic, foil, ampules, etc.). Other materials useful in the performance of the assays are included in the kits, including test tubes, transfer pipettes, and the like. In some cases, the kits also include written instructions for the use of one or more of these reagents in any of the assays described herein.

In some embodiments, kits also include a buffering agent, a preservative, or a protein/nucleic acid stabilizing agent. In some cases, kits also include other components of a reaction mixture as described herein. For example, kits include one or more aliquots of thermostable DNA polymerase as described herein, and/or one or more aliquots of dNTPs. In some cases, kits also include control samples of known amounts of template DNA molecules harboring the individual alleles of a locus. In some embodiments, the kit includes a negative control sample, e.g., a sample that does not contain DNA molecules harboring the individual alleles of a locus. In some embodiments, the kit includes a positive control sample, e.g., a sample containing known amounts of one or more of the individual alleles of a locus.

CERTAIN TERMINOLOGY

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

A "site" corresponds to a single site, which in some cases is a single base position or a group of correlated base positions, e.g., a CpG site. A "locus" corresponds to a region that includes multiple sites. In some instances, a locus includes one site.

EXAMPLES

These examples are provided for illustrative purposes only and not to limit the scope of the claims provided herein.

Example 1

Cell-free DNA sample was obtained from a QIAamp Circulating Nucleic Acid Kit. Methylation profile of biomarker cp10673833 (Cob-2) was used for the analysis.

Figure 2A:
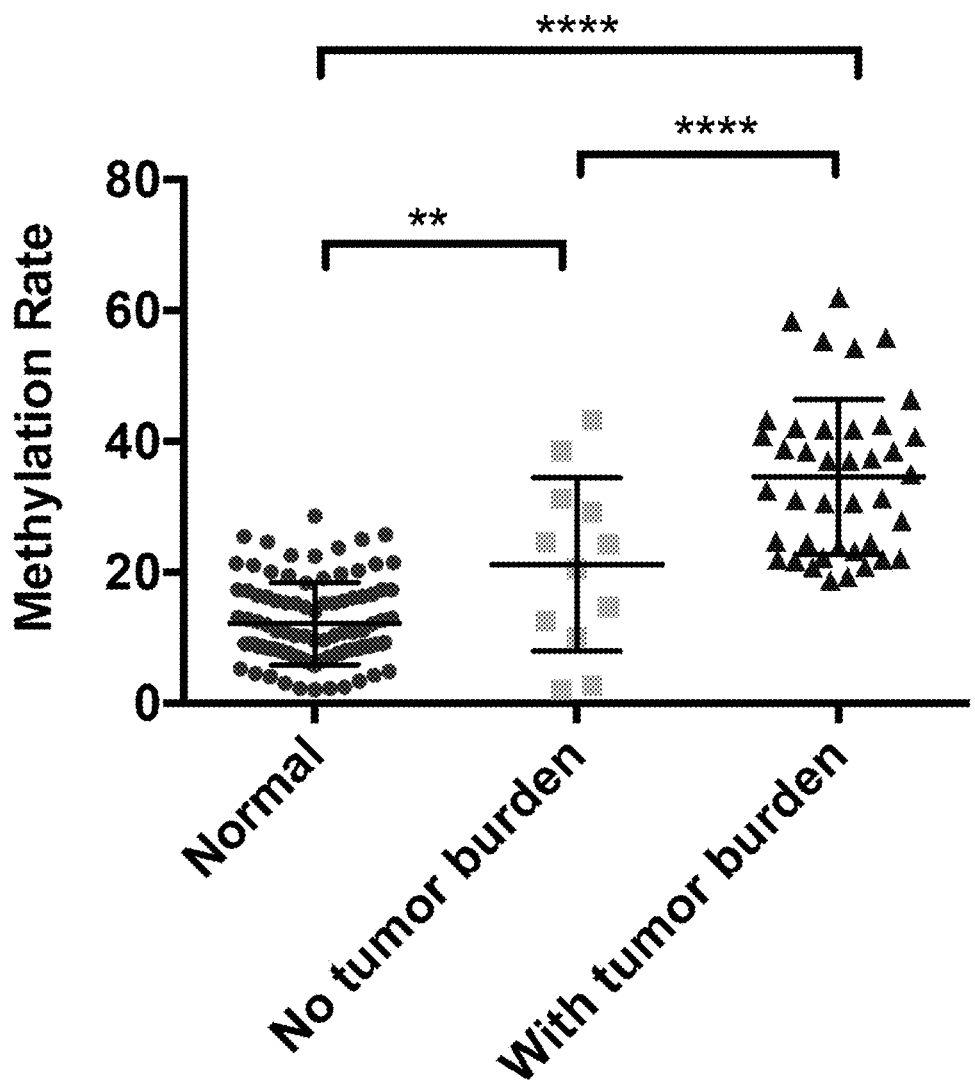
FIG. 2A-FIG. 2B illustrates the methylation rate of cell-free DNA (cfDNA) in different response groups for esophagus cancer.
Figure 2B:
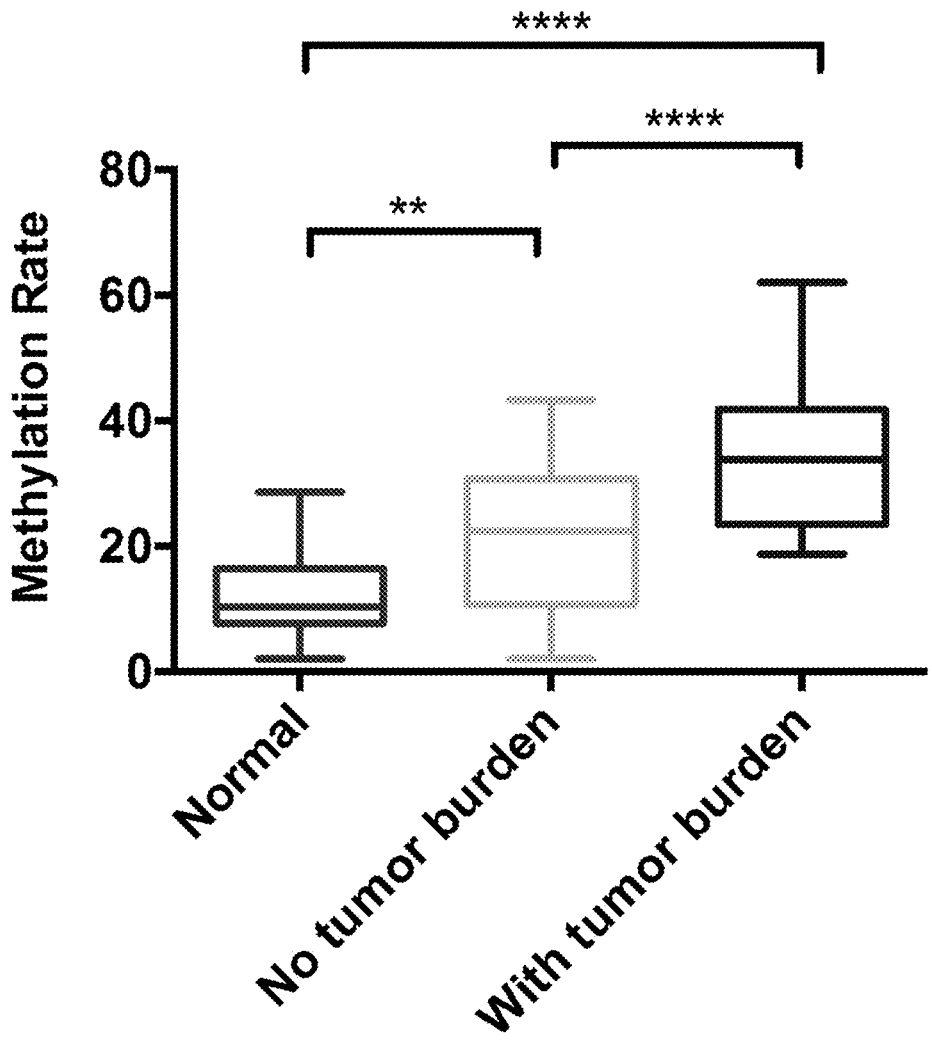
Figure 3A:
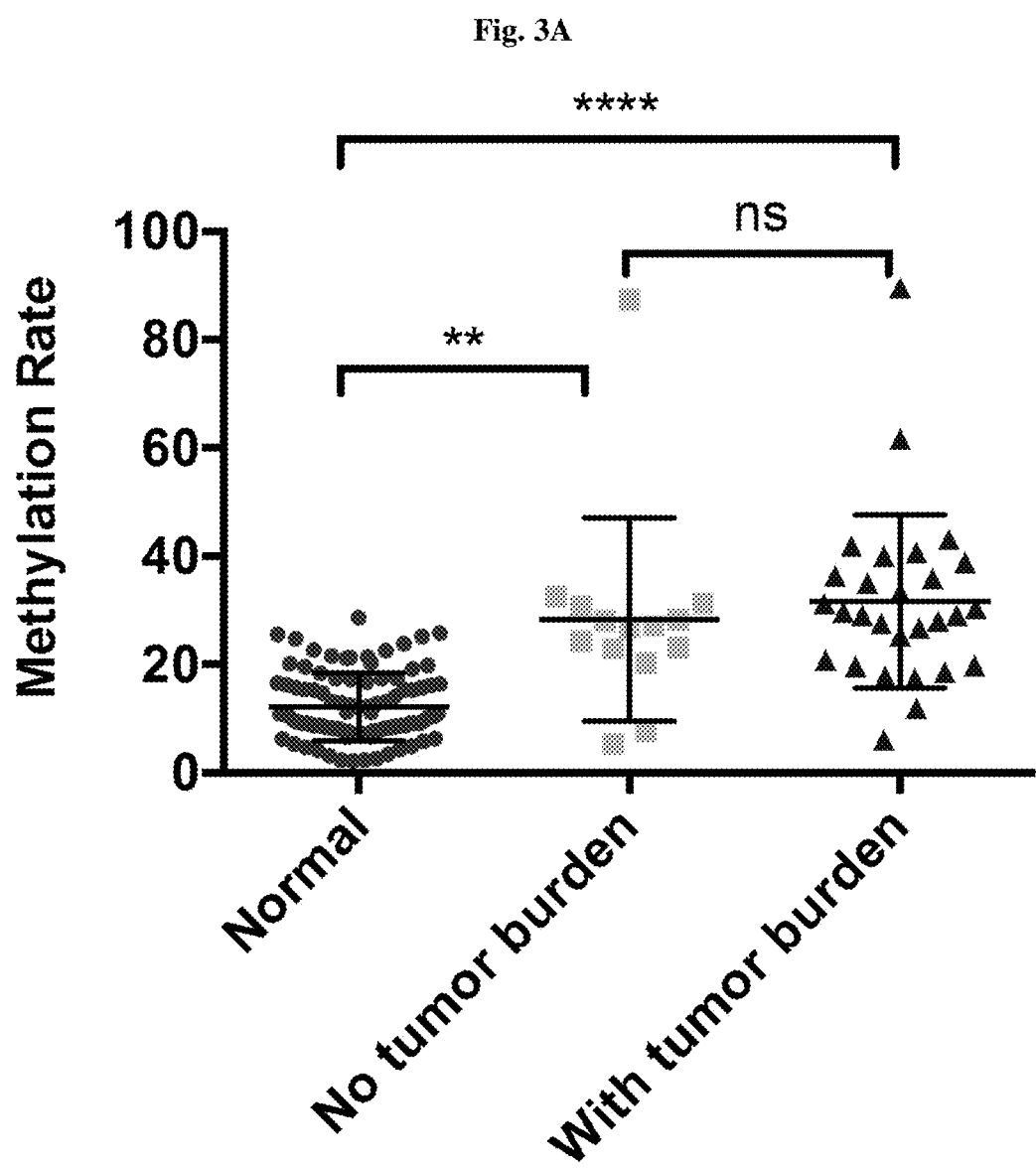
FIG. 3A-FIG. 3B illustrates the methylation rate of cell-free DNA (cfDNA) in different response groups for pancreatic cancer.
Figure 3B:
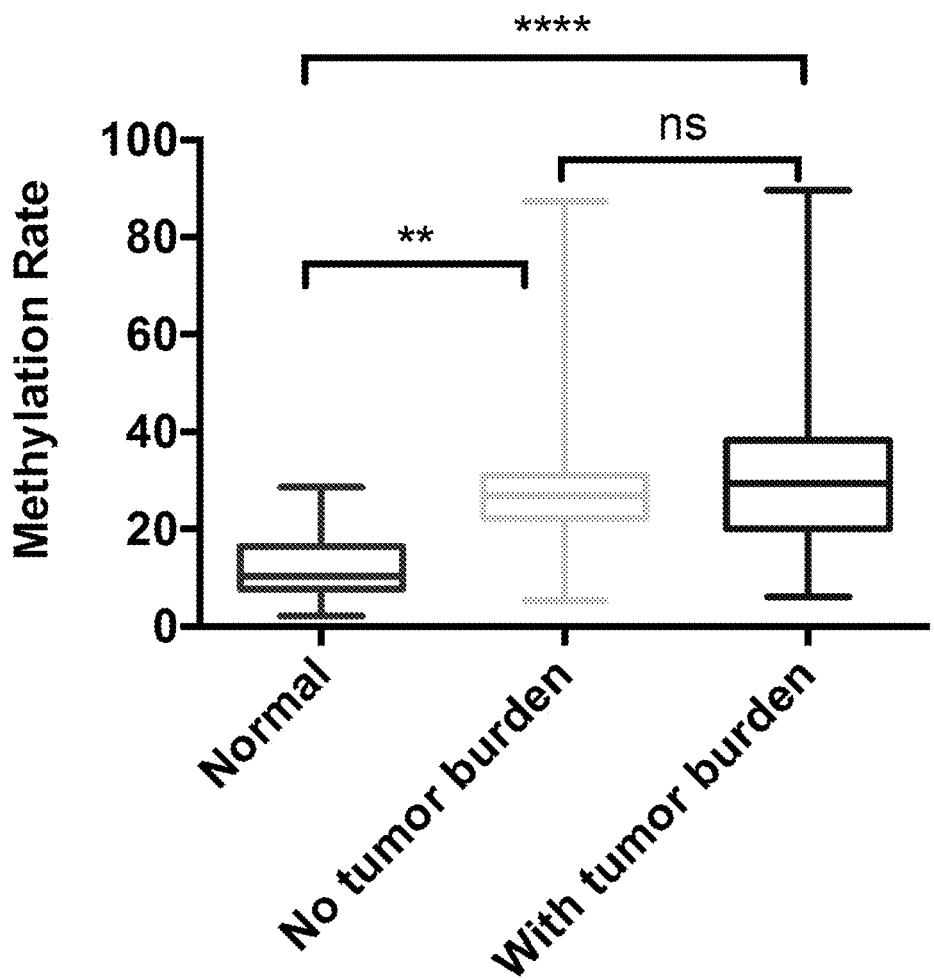
Figure 4A:
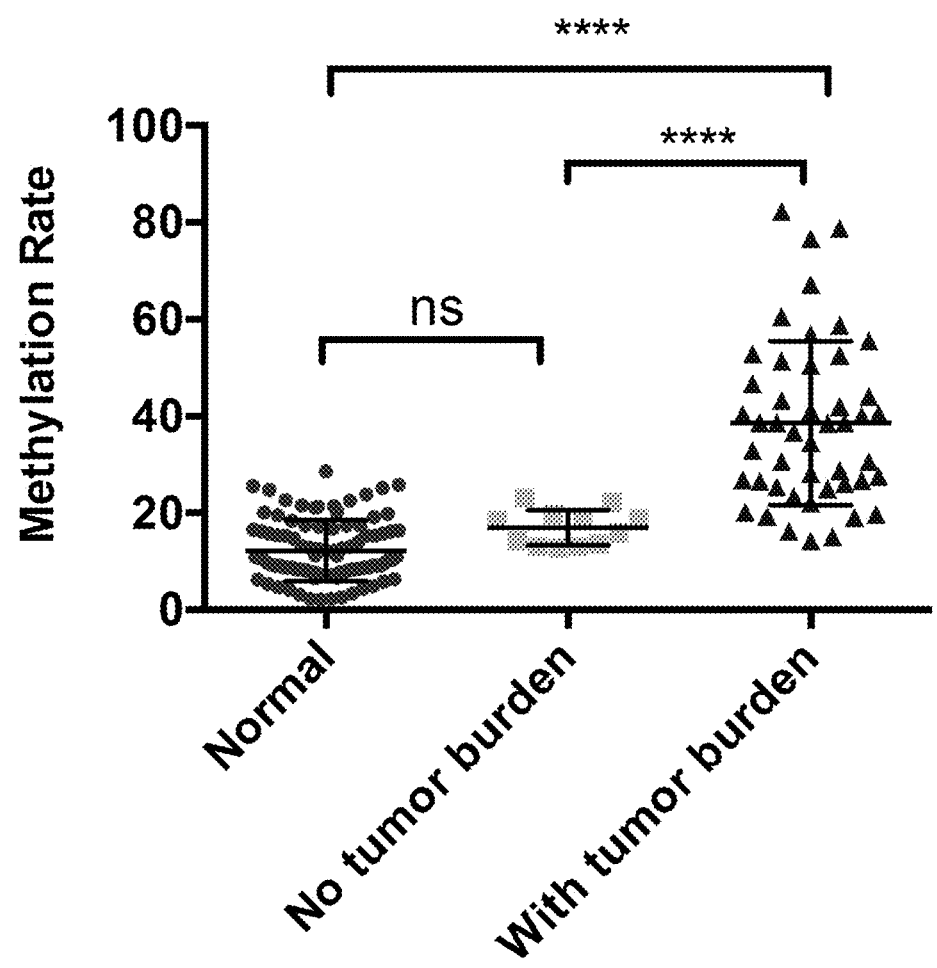
FIG. 4A-FIG. 4B illustrates the methylation rate of cell-free DNA (cfDNA) in different response groups for stomach cancer.
Figure 4B:
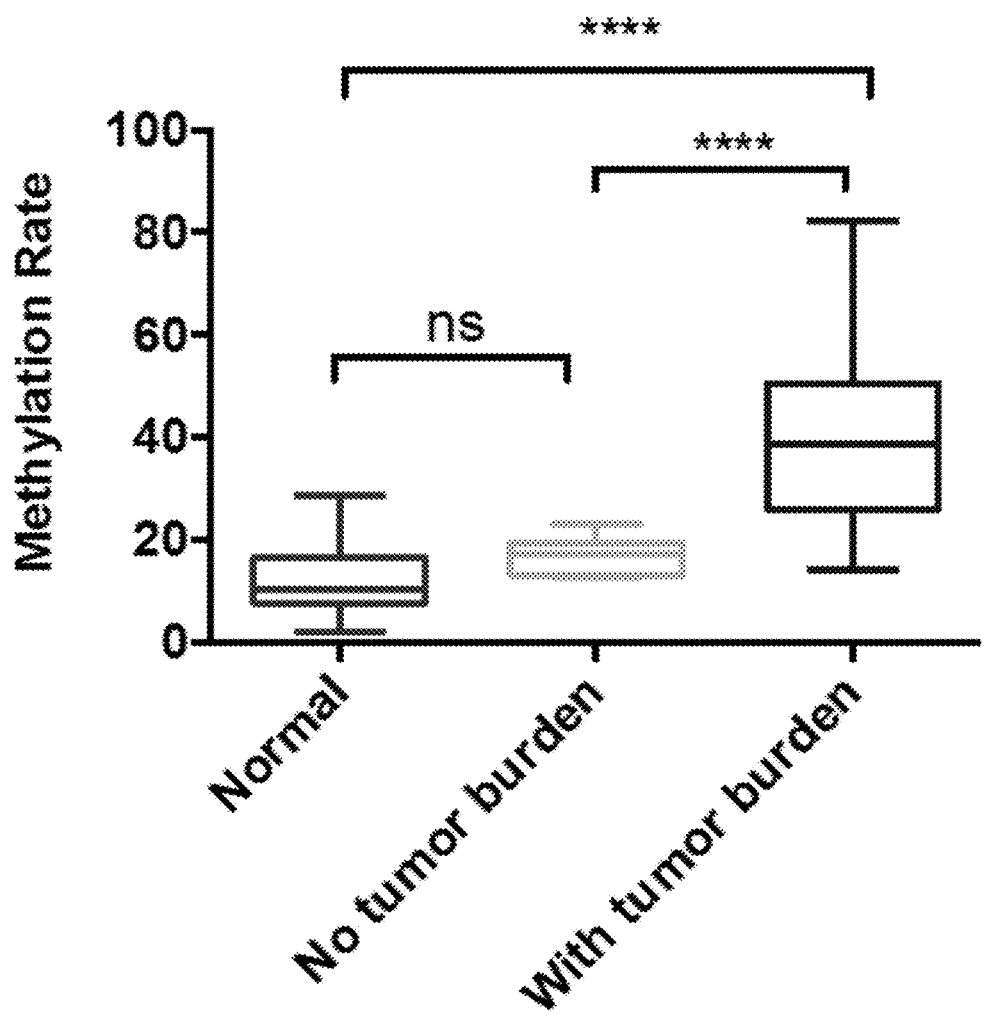

The methylation rate of Cob-2 from a subject having esophagus cancer, pancreatic cancer, or stomach cancer is higher relative to the methylation rate of Cob-2 from a normal subject (FIG. 1). Further, the methylation rate of Cob-2 differs between esophagus cancer, pancreatic cancer, and stomach cancer. Upon treatment, the rate of methylation is observed to decrease in the absence of tumor burden in all three cancer types: esophagus cancer (FIG. 2), pancreatic cancer (FIG. 3), and stomach cancer (FIG. 4). However, with the presence of tumor burden, the methylation rate is observed to be higher relative to the absence of tumor burden and normal sample (FIG. 2, FIG. 3, and FIG. 4).

Example 2. Identification of Methylation Correlated Block (MCB)

In some instances, closely positioned CpG have similar methylation levels, due to a processivity and lack of sequence-specificity of DNA methyltransferases and demethylases, as well as the concept of haplotype blocks in genetic linkage analysis. Pearson correlation coefficients r2 between β values of any two CpGs positioned within one kilobase of one another are calculated. A cutoff of r2>0.5 is used to identify Methylation Correlated Block (MCB) (also refers to herein as BCM) within regions interrogated by the padlock probes. A value of Pearson's r<0.5 is used to identify transition spots (boundaries) between any two adjacent markers indicating uncorrelated methylation. Markers not separated by a boundary are combined into Methylation Correlated Block (MCB). This procedure combines between 2 and 22 CpG positions in each block to identify a total number of BCMs in each diagnostic category within the padlock data. Methylation frequencies for entire MCBs are calculated by summing up the numbers of Cs at all interrogated CpG positions within a BCM and dividing by the total number of C+Ts at those positions Pearson correlation coefficients between methylation frequencies of each pair of CpG markers separated by no more than 200 bp are calculated separately from 30 cancer and 30 corresponding normal tissue samples from each of the two diagnostic categories. A value of Pearson's r<0.5 is used to identify transition spots (boundaries) between any two adjacent markers indicating uncorrelated methylation. Markers not separated by a boundary are combined into Methylation Correlated Block (MCB). Methylation frequencies for entire BCMs are calculated by summing up the numbers of Cs at all interrogated CpG positions within a BCM and dividing by the total number of C+Ts at those positions.

Example 3. Linking Differentially Methylated Markers to Gene Expression

TCGA DNA methylation and RNAseq expression data for pancreatic cancer samples are obtained from the TCGA website. The degree of DNA methylation at each CpG is denoted as a beta value and is calculated as (M/(M+U)), where M and U are normalized values representing the methylated and unmethylated allele intensities respectively. Beta values range from 0 to 1 and reflect the fraction of methylated alleles at each CpG in each sample. The methylation beta value is calculated for all 485,000 markers for each of the pancreatic cancer and matched normal sample in the TCGA data. CpG markers with a mean value less than 0.05 or greater than 0.95 are selected for further evaluation. Markers with a difference between the mean methylation value for the tumor tissue and the mean methylation value of the corresponding normal tissue of greater than 0.5 are also selected. At the intersection of these two groups, markers for which the mean methylation is <0.05 for normal samples and the difference between normal and tumor is greater than 0.5 are further selected and the genes associated with these markers are identified. For each marker, the pancreatic cancer samples are then separated into those with methylation values greater than the mean value of the pancreatic cancer samples and those with methylation values less than the mean value of the pancreatic cancer samples. Next, the RNAseq data in the TCGA data is examined and the relative expression of each gene is calculated. Because of the wide variation of the expression values, the values are adjusted as follows: log 2 (expressionValue+1). Genes are identified in which the difference in the methylation values correlated with variation in the associated gene expression levels. Genes for which there is a correlation were selected for further functional evaluation and validation.

DNA/RNA Isolation and Quantitative PCR

Leukemia and corresponding far site samples are obtained from patients; samples are frozen and preserved at −80° C. until use. Isolation of DNA and RNA from samples is performed using AllPrep DNA/RNA Mini kit (Qiagen, Valencia, Calif.) according to the manufacturer's recommendations. During RNA isolation, the sample is subjected to on-column DNase digestion. RNA is quantified using a Nanodrop 2000 (Thermo Scientific). 200 ng RNA of each sample is used for cDNA synthesis using iScript cDNA synthesis kit (Bio-rad, Inc) according to the manufacturer's instructions. qPCR is performed by a standard 40-cycle amplification protocol using gene-specific primers and a Power SYBR Green PCR Master Mix on a 7500 Real Time PCR system (Applied Biosystems). Experiments are carried out in triplicate and normalized to endogenous ACTB levels. Relative fold change in expression is calculated using the ΔΔCT method (cycle threshold values <30).

Cell Culture and Gene Transfections

Human pancreatic cancer cell line Panc 03.27 and the human embryonic kidney cell line HEK293a are obtained from American type culture collection (Manassas, Va., USA) and cultured according to their instructions. The expression construct for a gene disclosed herein is purchased from Origene in a form of TrueORF® cDNA clones in pCMV6-Entry vector. cDNAs are shuttled into pLenti-C-mGFP (Origene) to create a lentivector encoding a fusion protein between the desired gene and mGFP.

Lentiviral particles are made by co-transfection of HEK-293T cells with a pancreatic cancer gene mGFP lentivector together with a third-generation packaging vector using calcium phosphate precipitation. Viral supernatants are collected 36 hours post-transfection. Human pancreatic cancer cell line Panc 03.27 are plated in a 6-well plate the day before transfection of the leukemia gene mGFP lentivector. Stable cell lines are generated by infecting cells with viral particles at the MOI of ~5 for 24 hrs and are collected and sorted to 100% GFP—positivity using FACS. The GFP positive cells are then used for a colony formation assay in cell culture and tumor xenograft in nude mice.

Colony Formation Assays

Cells are plated in 6-well plates at a density of 500 cells per well and are cultured at 37° C. with 5% CO2 humidified air for 14 days. The colonies are fixed with 10% formaldehyde for 5 min and then stained with 0.1% crystal violet for 30 seconds. Colony consisting of 50 or more cells are counted. The experiment is performed in triplicate and repeated 3 times. Plate efficiency=(colony numbers/inoculated cell numbers)×100%.

Tumor Xenograft

All animal studies are performed in accordance with institutional and international animal regulations. Animal protocols are approved by the Institutional Animal Care and Use Committee of Sun Yat-Sen University. Female athymic BALB/c nude mice (4-5 weeks of age, 18-20 g) are purchased from a vendor (Guangdong Province Laboratory Animal Center, Guangzhou, China).

Mice are injected subcutaneously with 100 μl of tumor cells suspended in serum free medium. Tumor growth is monitored every 3 days by visual examination. Tumor sizes are measured using a caliper, and tumor volume is calculated according to the following equation: tumor volume (mm3)=(length (mm)×width (mm)2)×0.5. All animals are sacrificed 3-4 weeks postinjection and the xenografts were harvested. Representative data are obtained from five mice per experimental group. Statistical analyses are performed with one-way repeated-measures ANOVA.

Example 4

Table 1 illustrates the gene name referenced by the CpG site described herein.

| CpG Site | Genome_Build | CHR | MAP INFO | Chromosome_36 | Gene Coordinate_36 | Gene Name | Description | Alternative |
|---|---|---|---|---|---|---|---|---|
| cg10673833 | 37 | 7 | 45018849 | 7 | 44985374 | MYO1G | myosin IG | minor histocompatibility antigen HA-2, HA2, unconventional myosin-Ig, HLA-HA2, and MHAG |

Example 5

Table 2 illustrates the probe described herein.

| CpG Site | Gene | Sequence | SEQ ID NO: |
|---|---|---|---|
| cg10673833 | MYO1G | AACACAACCTCCTTATAAAACCTGTCTCTTA TACACATCTCCGAGCCCACGAGACTCGTCGG CAGCGTCAGATGTGTATAAGAGACAGNNNNN NAACIAAAAACCCTCCAAA | 1 |

Embodiment 1 refers to a method of generating a methylation profile of a biomarker in a subject in need thereof, comprising: (a) processing an extracted genomic DNA with a deaminating agent to generate a genomic DNA sample comprising deaminated nucleotides, wherein the extracted genomic DNA is obtained from a biological sample from the subject; (b) detecting a hybridization between the extracted genomic DNA and a probe, wherein the probe hybridizes to cg10673833 (myosin IG); and (c) generating a methylation profile based on the detected hybridization between the extracted genomic DNA and the probe.

Embodiment 2: the method of embodiment 1, wherein the probe comprises a structure of Formula I:

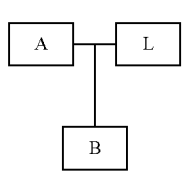

Formula I wherein:
A is a first target-binding region;
B is a second target-binding region; and
L is a linker region;
wherein A comprises at least 70%, 80%, 90%, 95%, or 99% sequence identity to at least 30 contiguous nucleotides starting at position 1 from the 5' terminus of SEQ ID NO: 1; B comprises at least 70%, 80%, 90%, 95%, or 99% sequence identity to at least 12 contiguous nucleotides starting at position 1' from the 3' terminus of SEQ ID NO: 1; and
wherein L is attached to A; and B is attached to either A or L.

Embodiment 3: the method of embodiment 2, wherein the probe comprises a structure of Formula Ia:

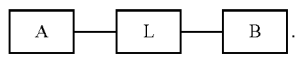

Formula Ia

Embodiment 4: the method of embodiment 2, wherein A comprises at least 70%, 80%, 90%, 95%, or 99% sequence identity to at least 40 contiguous nucleotides starting at position 1 from the 5' terminus of SEQ ID NO: 1.

Embodiment 5: the method of embodiment 2, wherein A comprises at least 70%, 80%, 90%, 95%, or 99% sequence identity to at least 50 contiguous nucleotides starting at position 1 from the 5' terminus of SEQ ID NO: 1.

Embodiment 6: the method of embodiment 2, wherein B comprises at least 70%, 80%, 90%, 95%, or 99% sequence identity to at least 15 contiguous nucleotides starting at position 1' from the 3' terminus of SEQ ID NO: 1.

Embodiment 7: the method of embodiment 2, wherein B comprises at least 70%, 80%, 90%, 95%, or 99% sequence identity to at least 20 contiguous nucleotides starting at position 1' from the 3' terminus of SEQ ID NO: 1.

Embodiment 8: the method of embodiment 2, wherein L is about 15, 20, 25, 30, 35, 40, 45, 50, 55, or 60 nucleotides in length.

Embodiment 9: the method of embodiment 1, wherein the probe comprises at least 80%, 85%, 90%, 91%, 92%, 93%, 94%, 95%, 96%, 97%, 98%, or 99% sequence identity to SEQ ID NO: 1.

Embodiment 10: the method of embodiment 1, wherein the generating further comprises generating a pair-wise methylation difference dataset comprising: (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

Embodiment 11: the method of embodiment 10, wherein the generating further comprises analyzing the pair-wise methylation difference dataset with a control by a machine learning method to generate the methylation profile.

Embodiment 12: the method of embodiment 10, wherein the first primary cancer sample is an esophagus cancer sample, a pancreatic cancer sample, or a stomach cancer sample.

Embodiment 13: the method of embodiment 10, wherein the second primary cancer sample is a non-esophagus cancer sample, non-pancreatic cancer sample, or a non-stomach cancer sample.

Embodiment 14: the method of embodiment 11, wherein the control comprises a set of methylation profiles, wherein each said methylation profile is generated from a biological sample obtained from a known cancer type.

Embodiment 15: the method of embodiment 14, wherein the known cancer type is esophagus cancer, pancreatic cancer, or stomach cancer.

Embodiment 16: the method of embodiment 14, wherein the known cancer type is a relapsed or refractory esophagus cancer, a relapsed or refractory pancreatic cancer, or a relapsed or refractory stomach cancer.

Embodiment 17: the method of embodiment 14, wherein the known cancer type is a metastatic esophagus cancer, a metastatic pancreatic cancer, or a metastatic stomach cancer.

Embodiment 18: the method of embodiment 14, where the known cancer type is esophagus cancer.

Embodiment 19: the method of embodiment 18, wherein esophagus cancer comprises esophageal squamous cell carcinoma, esophageal adenocarcinoma, or undifferentiated esophagus cancer.

Embodiment 20: the method of embodiment 14, where the known cancer type is pancreatic cancer.

Embodiment 21: the method of embodiment 20, wherein pancreatic cancer comprises exocrine pancreatic cancers and pancreatic endocrine tumors.

Embodiment 22: the method of embodiment 20, wherein pancreatic cancer comprises pancreatic adenocarcinoma, pancreatic adenosquamous carcinomas, pancreatic squamous cell carcinomas, signet ring cell carcinomas, undifferentiated pancreatic carcinomas, undifferentiated pancreatic carcinomas with giant cells, ampullary cancer, gastrinomas, insulinomas, glucagonomas, somatostatinomas, VIPomas, PPomas, or carcinoid tumor.

Embodiment 23: the method of embodiment 14, where the known cancer type is stomach cancer.

Embodiment 24: the method of embodiment 23, wherein stomach cancer comprises gastric adenocarcinoma, lymphoma of the stomach, gastrointestinal stromal tumor, carcinoid tumor, primary squamous cell carcinoma of stomach, gastric small-cell carcinoma, or leiomyosarcoma of the stomach.

Embodiment 25: the method of embodiment 11, wherein the machine learning method utilizes an algorithm selected from one or more of the following: a principal component analysis, a logistic regression analysis, a nearest neighbor analysis, a support vector machine, and a neural network model.

Embodiment 26: the method of any one of the embodiments 1-25, wherein the method further comprises performing a DNA sequencing reaction to quantify the methylation of the biomarker prior to generating the methylation profile.

Embodiment 27 refers to a method of selecting a subject suspected of having a solid tumor for treatment, the method comprising: (a) processing an extracted genomic DNA with a deaminating agent to generate a genomic DNA sample comprising deaminated nucleotides, wherein the extracted genomic DNA is obtained from a biological sample from the subject suspected of having a solid tumor; (b) generating a methylation profile comprising cg10673833 (myosin IG) from the extracted genomic DNA; (c) comparing the methylation profile of the biomarker with a control; (d) identifying the subject as having the solid tumor if the methylation profile correlates to the control; and (e) administering an effective amount of a therapeutic agent to the subject if the subject is identified as having the solid tumor; wherein the solid tumor is selected from esophagus cancer, pancreatic cancer, or stomach cancer.

Embodiment 28: the method of embodiment 27, wherein the probe comprises a structure of Formula I:

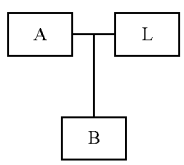

Formula I wherein:
A is a first target-binding region;
B is a second target-binding region; and
L is a linker region;
wherein A comprises at least 70%, 80%, 90%, 95%, or 99% sequence identity to at least 30 contiguous nucleotides starting at position 1 from the 5' terminus of SEQ ID NO: 1; B comprises at least 70%, 80%, 90%, 95%, or 99% sequence identity to at least 12 contiguous nucleotides starting at position 1' from the 3' terminus of SEQ ID NO: 1; and
wherein L is attached to A; and B is attached to either A or L.

Embodiment 29: the method of embodiment 28, wherein the probe comprises a structure of Formula Ia:

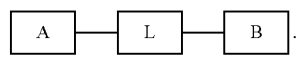

Formula Ia

Embodiment 30: the method of embodiment 28, wherein A comprises at least 70%, 80%, 90%, 95%, or 99% sequence identity to at least 40 contiguous nucleotides starting at position 1 from the 5' terminus of SEQ ID NO: 1.

Embodiment 31: the method of embodiment 28, wherein A comprises at least 70%, 80%, 90%, 95%, or 99% sequence identity to at least 50 contiguous nucleotides starting at position 1 from the 5' terminus of SEQ ID NO: 1.

Embodiment 32: the method of embodiment 28, wherein B comprises at least 70%, 80%, 90%, 95%, or 99% sequence identity to at least 15 contiguous nucleotides starting at position 1' from the 3' terminus of SEQ ID NO: 1.

Embodiment 33: the method of embodiment 28, wherein B comprises at least 70%, 80%, 90%, 95%, or 99% sequence identity to at least 20 contiguous nucleotides starting at position 1' from the 3' terminus of SEQ ID NO: 1.

Embodiment 34: the method of embodiment 28, wherein L is about 15, 20, 25, 30, 35, 40, 45, 50, 55, or 60 nucleotides in length.

Embodiment 35: the method of embodiment 27, wherein the probe comprises at least 80%, 85%, 90%, 91%, 92%, 93%, 94%, 95%, 96%, 97%, 98%, or 99% sequence identity to SEQ ID NO: 1.

Embodiment 36: the method of embodiment 27, wherein the comparing further comprises generating a pair-wise methylation difference dataset comprising: (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

Embodiment 37: the method of embodiment 27 or 36, wherein the comparing further comprises analyzing the pair-wise methylation difference dataset with a control by a machine learning method to generate the methylation profile.

Embodiment 38: the method of embodiment 36, wherein the first primary cancer sample is an esophagus cancer sample, a pancreatic cancer sample, or a stomach cancer sample.

Embodiment 39: the method of embodiment 36, wherein the second primary cancer sample is a non-esophagus cancer sample, non-pancreatic cancer sample, or a non-stomach cancer sample.

Embodiment 40: the method of embodiment 37, wherein the control comprises a set of methylation profiles, wherein each said methylation profile is generated from a biological sample obtained from a known cancer type.

Embodiment 41: the method of embodiment 40, wherein the known cancer type is esophagus cancer, pancreatic cancer, or stomach cancer.

Embodiment 42: the method of embodiment 40 or 41, wherein the known cancer type is a relapsed or refractory esophagus cancer, a relapsed or refractory pancreatic cancer, or a relapsed or refractory stomach cancer.

Embodiment 43: the method of any one of the embodiments 40-42, wherein the known cancer type is a metastatic esophagus cancer, a metastatic pancreatic cancer, or a metastatic stomach cancer.

Embodiment 44: the method of embodiment 37, wherein the machine learning method utilizes an algorithm selected from one or more of the following: a principal component analysis, a logistic regression analysis, a nearest neighbor analysis, a support vector machine, and a neural network model.

Embodiment 45: the method of any one of the embodiments 27-44, wherein the generating further comprises hybridizing the biomarker with a probe, and performing a DNA sequencing reaction to quantify the methylation of the biomarker.

Embodiment 46: the method of any one of the embodiments 1-45, wherein the biological sample comprises circulating tumor cells.

Embodiment 47: the method of any one of the embodiments 1-46, wherein the subject is a human.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

wherein the probe comprises a structure of Formula I:

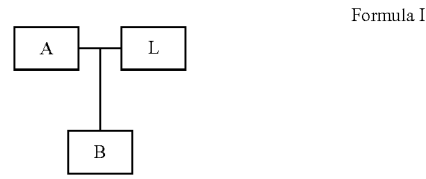

Formula I wherein:
  A is a first target-binding region;
  B is a second target-binding region; and
  L is a linker region;
  wherein A comprises at least 30 contiguous nucleotides starting at position 1 from the 5' terminus of SEQ ID NO: 1; B comprises at least 12 contiguous nucleotides starting at position 1' from the 3' terminus of SEQ ID NO: 1; and
  wherein L is attached to A; and B is attached to either A or L.

2. The method of claim 1, wherein the probe comprises a structure of Formula Ia:

What is claimed is:

1. A method of generating a methylation profile of a biomarker in a subject in need thereof, comprising:
  a) processing an extracted genomic DNA with a deaminating agent to generate a genomic DNA sample comprising deaminated nucleotides, wherein the extracted genomic DNA is obtained from a biological sample from the subject;
  b) detecting a hybridization between the extracted genomic DNA and a probe, wherein the probe hybridizes to cg10673833 (myosin IG); and
  c) generating a methylation profile based on the detected hybridization between the extracted genomic DNA and the probe;

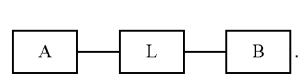

Formula Ia

3. The method of claim 1, wherein A comprises at least 40 contiguous nucleotides starting at position 1 from the 5' terminus of SEQ ID NO: 1.

4. The method of claim 1, wherein A comprises at least 50 contiguous nucleotides starting at position 1 from the 5' terminus of SEQ ID NO: 1.

5. The method of claim 1, wherein B comprises at least 15 contiguous nucleotides starting at position 1' from the 3' terminus of SEQ ID NO: 1.

6. The method of claim 1, wherein B comprises at least 20 contiguous nucleotides starting at position 1' from the 3' terminus of SEQ ID NO: 1.

7. The method of claim 1, wherein L is about 15, 20, 25, 30, 35, 40, 45, 50, 55, or 60 nucleotides in length.

8. The method of claim 1, wherein the probe comprises SEQ ID NO: 1.

9. The method of claim 1, wherein the generating further comprises generating a pair-wise methylation difference dataset comprising:
(i) a first difference between the methylation profile of the treated genomic DNA with a methylation profile of a first normal sample;
(ii) a second difference between a methylation profile of a second normal sample and a methylation profile of a third normal sample; and
(iii) a third difference between a methylation profile of a first primary cancer sample and a methylation profile of a second primary cancer sample.

10. The method of claim 9, wherein the generating further comprises analyzing the pair-wise methylation difference dataset with a control by a machine learning method to generate the methylation profile.

11. The method of claim 9, wherein the first primary cancer sample is an esophagus cancer sample, a pancreatic cancer sample, or a stomach cancer sample.

12. The method of claim 9, wherein the second primary cancer sample is a non-esophagus cancer sample, non-pancreatic cancer sample, or a non-stomach cancer sample.

13. The method of claim 10, wherein the control comprises a set of methylation profiles, wherein each said methylation profile is generated from a biological sample obtained from a known cancer type.

14. The method of claim 13, wherein the known cancer type is esophagus cancer, pancreatic cancer, or stomach cancer.

15. The method of claim 13, wherein the known cancer type is a relapsed or refractory esophagus cancer, a relapsed or refractory pancreatic cancer, or a relapsed or refractory stomach cancer.

16. The method of claim 13, wherein the known cancer type is a metastatic esophagus cancer, a metastatic pancreatic cancer, or a metastatic stomach cancer.

17. The method of claim 13, where the known cancer type is esophagus cancer.

18. The method of claim 17, wherein esophagus cancer comprises esophageal squamous cell carcinoma, esophageal adenocarcinoma, or undifferentiated esophagus cancer.

19. The method of claim 13, where the known cancer type is pancreatic cancer.

20. The method of claim 19, wherein pancreatic cancer comprises exocrine pancreatic cancers and pancreatic endocrine tumors.

21. The method of claim 19, wherein pancreatic cancer comprises pancreatic adenocarcinoma, pancreatic adenosquamous carcinomas, pancreatic squamous cell carcinomas, signet ring cell carcinomas, undifferentiated pancreatic carcinomas, undifferentiated pancreatic carcinomas with giant cells, ampullary cancer, gastrinomas, insulinomas, glucagonomas, somatostatinomas, VIPomas, PPomas, or carcinoid tumor.

22. The method of claim 13, where the known cancer type is stomach cancer.

23. The method of claim 22, wherein stomach cancer comprises gastric adenocarcinoma, lymphoma of the stomach, gastrointestinal stromal tumor, carcinoid tumor, primary squamous cell carcinoma of stomach, gastric small-cell carcinoma, or leiomyosarcoma of the stomach.

24. The method of claim 10, wherein the machine learning method utilizes an algorithm selected from one or more of the following: a principal component analysis, a logistic regression analysis, a nearest neighbor analysis, a support vector machine, and a neural network model.

25. The method of claim 1, wherein the method further comprises performing a DNA sequencing reaction to quantify the methylation of the biomarker prior to generating the methylation profile.

26. A method of selecting a subject suspected of having a solid tumor for treatment, the method comprising:
a) processing an extracted genomic DNA with a deaminating agent to generate a genomic DNA sample comprising deaminated nucleotides, wherein the extracted genomic DNA is obtained from a biological sample from the subject suspected of having a solid tumor;
b) generating a methylation profile comprising cg10673833 (myosin IG) from the extracted genomic DNA, wherein the generating comprises detecting a hybridization between the extracted genomic DNA and a probe that hybridizes to cg10673833 (myosin IG);
c) comparing the methylation profile comprising cg10673833 with a control;
d) identifying the subject as having the solid tumor if the methylation profile correlates to the control; and
e) administering an effective amount of a therapeutic agent to the subject if the subject is identified as having the solid tumor;
wherein the solid tumor is selected from esophagus cancer, pancreatic cancer, or stomach cancer; and
wherein the probe comprises a structure of Formula I:

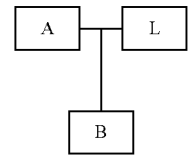

Formula I wherein:
A is a first target-binding region;
B is a second target-binding region; and
L is a linker region;
wherein A comprises at least 30 contiguous nucleotides starting at position 1 from the 5' terminus of SEQ ID NO: 1; B comprises at least 12 contiguous nucleotides starting at position 1' from the 3' terminus of SEQ ID NO: 1; and
wherein L is attached to A; and B is attached to either A or L.

* * * * *

SEQUENCE LISTING

```
<160> NUMBER OF SEQ ID NOS: 1

<210> SEQ ID NO 1
<211> LENGTH: 112
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (89)..(94)
<223> OTHER INFORMATION: a, c, t, g, unknown or other
<220> FEATURE:
<221> NAME/KEY: modified_base
<222> LOCATION: (98)..(98)
<223> OTHER INFORMATION: Inosine

<400> SEQUENCE: 1
aacacaacct ccttataaaa cctgtctctt atacacatct ccgagcccac gagactcgtc      60
ggcagcgtca gatgtgtata agagacagnn nnnnaacnaa aaaccctcca aa            112
```